(12) United States Patent
De Crescenzo et al.

(10) Patent No.: US 7,786,261 B2
(45) Date of Patent: Aug. 31, 2010

(54) COILED-COIL FUSION PROTEINS COMPRISING CELL RECEPTOR DOMAINS

(75) Inventors: Gregory De Crescenzo, Montreal (CA); Maureen D. O'Conner, Beaconsfield (CA); Beatrice Paul-Roc, Montreal (CA); John Zwaagstra, Laval (CA); Myriam Banville, Laval (CA); Maria Jaramillo, Beaconsfield (CA)

(73) Assignee: National Research Council of Canada, Ottawa, ON (CA)

( * ) Notice: Subject to any disclaimer, the term of this patent is extended or adjusted under 35 U.S.C. 154(b) by 747 days.

(21) Appl. No.: 10/570,412

(22) PCT Filed: Sep. 2, 2004

(86) PCT No.: PCT/CA2004/001616

§ 371 (c)(1),
(2), (4) Date: Nov. 21, 2006

(87) PCT Pub. No.: WO2005/024035

PCT Pub. Date: Mar. 17, 2005

(65) Prior Publication Data

US 2007/0154994 A1 Jul. 5, 2007

Related U.S. Application Data

(60) Provisional application No. 60/500,855, filed on Sep. 5, 2003.

(51) Int. Cl.
*C07K 1/00* (2006.01)
*C07K 14/00* (2006.01)
*C07K 17/00* (2006.01)
*C12P 21/06* (2006.01)
*C12N 1/20* (2006.01)
*C12N 15/00* (2006.01)
*C12N 5/00* (2006.01)
*C12N 5/02* (2006.01)
*C12N 15/74* (2006.01)
*C07H 21/04* (2006.01)

(52) U.S. Cl. .................. 530/350; 435/69.7; 435/252.3; 435/320.1; 435/325; 435/471; 435/810; 435/975; 536/23.5

(58) Field of Classification Search .................. None
See application file for complete search history.

(56) References Cited

U.S. PATENT DOCUMENTS

| | | | |
|---|---|---|---|
| 5,719,060 A | 2/1998 | Hutchens et al. | |
| 5,844,099 A | 12/1998 | Stahl et al. | |
| 6,020,208 A | 2/2000 | Hutchens et al. | |
| 6,027,942 A | 2/2000 | Hutchens et al. | |
| 6,197,599 B1 | 3/2001 | Chin et al. | |
| 6,322,970 B1 | 11/2001 | Little et al. | |
| 6,380,365 B1 | 4/2002 | Akerstrom et al. | |
| 6,395,494 B1 * | 5/2002 | Grainger et al. | 435/7.1 |
| 6,472,179 B2 | 10/2002 | Stahl et al. | |
| 6,787,368 B1 | 9/2004 | Wong et al. | |
| 6,800,453 B2 | 10/2004 | Labaer et al. | |

FOREIGN PATENT DOCUMENTS

| | | |
|---|---|---|
| CA | 2 345 109 A1 | 4/2000 |
| CA | 2 362 541 A1 | 8/2000 |
| WO | WO97/12988 | 4/1997 |
| WO | WO97/41424 | 11/1997 |
| WO | WO00/52456 A1 | 9/2000 |

OTHER PUBLICATIONS

Stratagene Catalog, p. 39, 1988.*
Letourneur O et al. Biochem. Biophys. Res. Comm. 224:709-716, 1996.*
Anders et al., *Journal of Biol. Chem.*, 271(36):21758-21766 (1996).
Hays et al., *Journal of Biol. Chem.*, 278(30):27456-27463 (2003).
Behncken et al., *Journal of Biol. Chem.*, 275(22):17000-17007 (2000).
Cochran et al., *Science*, 271(5252):1113-1116 (1996).
Chao, H., et al., *Biochemistry* 35(37):12175-12185 (1996).
Chao, H., et al., "Use of heterodimeric coiled-coil system for biosensor application and affinity purification," *J. of Chromatog. B*, 715:1 307-329 (1998).
De Crescenzo et al., *J. Mol. Biol.*, 32(5):1173-1183 (2003).
De Crescenzo et al., *Biochemistry*, 42(6):1754-1763 (2003).
De Crescenzo et al., *J. Mol. Biol.*, 279(25):26013-26018 (2004).
Hodges et al., *Biochemistry Cell Biol.*, 74(2):133-154 (1996).
Houston, Jr., M.E., et al., *J. Mol. Biol.*, 262:270-282 (1996).
Kodadek, T., "Protein microarrays: prospects and problems," *Chemistry and Biology*, 8:2 105-115 (2001).
Kohn et al., *The Journal of Biological Chemistry*, 272(5):2583-2586 (1997).
Matsumoto et al., *PNAS USA*, 87(23):9133-9137 (1990).
Nedelkov, D., *Proteomics*, 1:1441-1446 (2001).
Nelson, R.W., et al., "Biosensor chip mass spectrometry: A chip-based proteomics approach," *Electrophoresis*, 21:1155-1163 (2000).
Pagano et al., *J. Neurosci.*, 21(4):1189-1202 (2001).
Tripet, B., et al., *Protein Engineering* 9(11):1029-1042, (1996).
Woolfson, Derek, *Advances in Protein Chemistry*, 70:79-112 (2005).
Yang et al., *J.Clin. Inves.*, 109(12):1607-1615 (2002).
Zhang, Y., et al., *Biochemistry* 40(2):474-482, (2001).

* cited by examiner

*Primary Examiner*—Robert Landsman
(74) *Attorney, Agent, or Firm*—Hans Koenig

(57) ABSTRACT

Fusion proteins and coiled-coil induced dimers prepared from both the ectodomains and the kinase domains are disclosed. The receptor domains when presented in the form of a homodimer or heterodimer by virtue of the coiled-coil tag have enhanced ligand binding activity or enhanced kinase activity. The kinetics of binding and the antagonistic potencies of the ectodomain dimers, and their use to alter or inhibit signaling is described. Application of the ectodomain and kinase domain dimers in assays for selecting compounds capable of inhibiting ligand binding and kinase activity, respectively, is described.

16 Claims, 13 Drawing Sheets

```
1               20                40                60
|               |                 |                 |
MGRGLLRGLWPLHIVLWTRIASTIPPEQKLISEEDLLHVQKSVNNDMIVTDNNGAVKFPQ
  TβRIIED            myc tag
LCKFCDVRFSTCDNQKSCMSNCSITSICEKPQEVCVAVWRKNDENITLETVCHDPKLPYH
                       TβRIIED
DFILEDAASPKCIMKEKKKPGETFFMCSCSSDECNDNIIFSEEYNTSNPDGGRGGGGSGG
                                                   Linker
GEVSALEKEVSALEKEVSALEKEVSALEKEVSALEKGGHHHHHH Stop
    E5 Coil                                  His Tag
```

Fig. 1A

```
1               20                40                60
|               |                 |                 |
MGRGLLRGLWPLHIVLWTRIASTIPPEQKLISEEDLLHVQKSVNNDMIVTDNNGAVKFPQ
  TβRIIED            myc tag
LCKFCDVRFSTCDNQKSCMSNCSITSICEKPQEVCVAVWRKNDENITLETVCHDPKLPYH
                       TβRIIED
DFILEDAASPKCIMKEKKKPGETFFMCSCSSDECNDNIIFSEEYNTSNPDGGRGGGGSGG
                                                   Linker
GKVSALKEKVSALKEKVSALKEKVSALKEKVSALKEGGHHHHHH Stop
    K5 Coil                                  His Tag
```

Fig. 1B

```
1               20                40                60
|               |                 |                 |
MAVTSHHMIPVMVVLMSACLATAGPEQKLISEEDLRQLRNPSGFQGQLDGNATFNMELYN
  TβRIIED              myc tag
TDLFLVPSPGVFSVAENEHVYVEVSVTKADQDLGFAIQTCFLSPYSNPDRMSDYTIIENI
                       TβRIIED
CPKDDSVKFYSSKRVHFPIPHAEVDKKRFSFLFKSVFNTSLLFLHCELTLCSRKKGSLKL

PRCVTPDDACTSLDATMIWTMMQNKKTFTKPLAVVLQVDYKENVPSTKDSSPIPPPPPQI

FHGGRGGGGSGGGKVSALKEKVSALKEKVSALKEKVSALKEKVSALKEGGHHHHHH Stop
    Linker            K5 Coil                      His tag
```

Fig. 1C

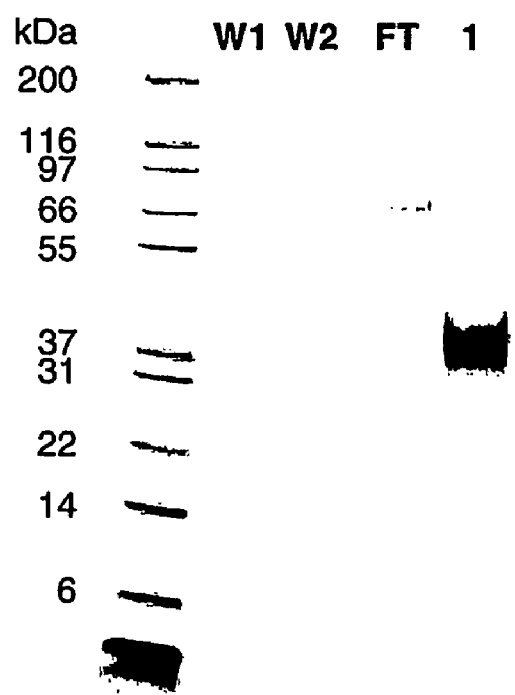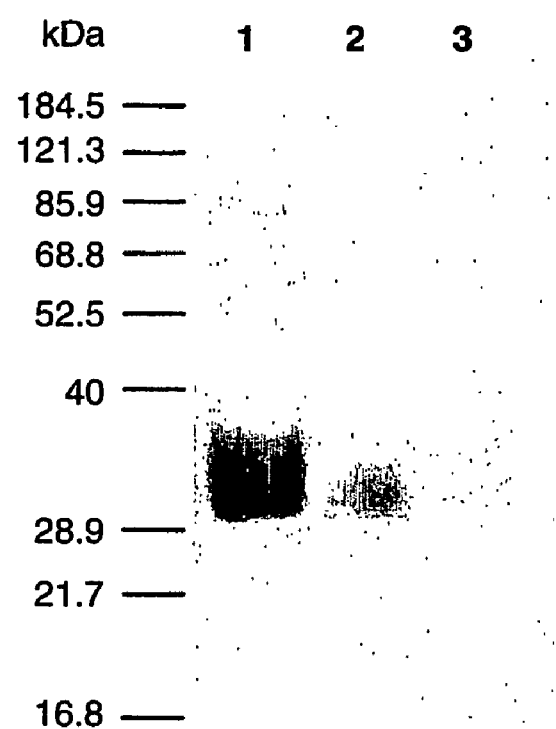
Fig. 2A                    Fig. 2B

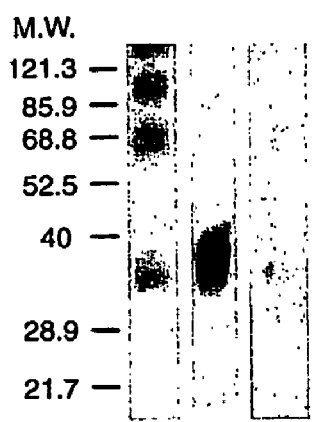
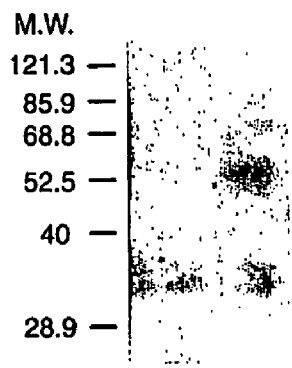
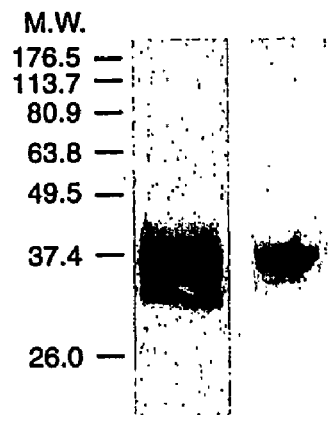
Fig. 3A  Fig. 3B  Fig. 3C  Fig. 3D  Fig. 3E  Fig. 3F  Fig. 3G

| | | | | | | | | | | | | | | | | | | | | |
|---|---|---|---|---|---|---|---|---|---|---|---|---|---|---|---|---|---|---|---|---|
|1|<u>M</u>|<u>G</u>|<u>G</u>|<u>G</u>|<u>G</u>|<u>G</u>|K|V|S|A|L|K|E|K|V|S|A|L|K|E|
|21|K|V|S|A|L|K|E|K|V|S|A|L|K|E|K|V|S|A|L|K|
|41|E|<u>G</u>|<u>G</u>|<u>G</u>|<u>G</u>|<u>S</u>|<u>L</u>|<u>E</u>|R|R|R|H|I|V|R|K|R|T|L|R|
|61|R|L|L|Q|E|R|E|L|V|E|P|L|T|P|S|G|E|A|P|N|
|81|Q|A|L|L|R|I|L|K|E|T|E|F|K|K|I|K|V|L|G|S|
|101|G|A|F|G|T|V|Y|K|G|L|W|I|P|E|G|E|K|V|K|I|
|121|P|V|A|I|K|E|L|R|E|A|T|S|P|K|A|N|K|E|I|L|
|141|D|E|A|Y|V|M|A|S|V|D|N|P|H|V|C|R|L|L|G|I|
|161|C|L|T|S|T|V|Q|L|I|T|Q|L|M|P|F|G|C|L|L|D|
|181|Y|V|R|E|H|K|D|N|I|G|S|Q|Y|L|L|N|W|C|V|Q|
|201|I|A|K|G|M|N|Y|L|E|D|R|R|L|V|H|R|D|L|A|A|
|221|R|N|V|L|V|K|T|P|Q|H|V|K|I|T|D|F|G|L|A|K|
|241|L|L|G|A|E|E|K|E|Y|H|A|E|G|G|K|V|P|I|K|W|
|261|M|A|L|E|S|I|L|H|R|I|Y|T|H|Q|S|D|V|W|S|Y|
|281|G|V|T|V|W|E|L|M|T|F|G|S|K|P|Y|D|G|I|P|A|
|301|S|E|I|S|S|I|L|E|K|G|E|R|L|P|Q|P|P|I|C|T|
|321|I|D|V|Y|M|I|M|V|K|C|W|M|I|D|A|D|S|R|P|K|
|341|F|R|E|L|I|I|E|F|S|K|M|A|R|D|P|Q|R|Y|L|V|
|361|I|Q|G|D|E|R|M|H|L|P|S|P|T|D|S|N|F|Y|R|A|
|381|L|M|D|E|E|D|M|D|D|V|V|D|A|D|E|Y|L|I|P|Q|
|401|Q|G|F|F|S|S|P|S|T|S|R|T|P|L|L|S|S|L|S|A|
|421|T|S|N|N|S|T|V|A|C|I|D|R|N|G|L|Q|S|C|P|I|
|441|K|E|D|S|F|L|Q|R|Y|S|S|D|P|T|G|A|L|T|E|D|
|461|S|I|D|D|T|F|L|P|V|P|E|Y|I|N|Q|S|V|P|K|R|
|481|P|A|G|S|V|Q|N|P|V|Y|H|N|Q|P|L|N|P|A|P|S|
|501|R|D|P|H|Y|Q|D|P|H|S|T|A|V|G|N|P|E|Y|L|N|
|521|T|V|Q|P|T|C|V|N|S|T|F|D|S|P|A|H|W|A|Q|K|
|541|G|S|H|Q|I|S|L|D|N|P|D|Y|Q|Q|D|F|F|P|K|E|
|561|A|K|P|N|G|I|F|K|G|S|T|A|E|N|A|E|Y|L|R|V|
|581|A|P|Q|S|S|E|F|I|G|A|<u>H</u>|<u>H</u>|<u>H</u>|<u>H</u>|<u>H</u>|<u>H</u>| | | | |

COILED-COIL FUSION PROTEINS COMPRISING CELL RECEPTOR DOMAINS

This application is a 35 USC §371 application of International Application No. PCT/CA2004/001616 filed Sep. 2, 2004, designating the United States; which claims priority to U.S. Provisional Application No. 60/500,855 filed Sep. 5, 2003, now abandoned, both of which are hereby incorporated by reference in their entirety.

FIELD OF THE INVENTION

The present invention relates in general to compositions and methods of use of a fusion protein comprised of a domain of a cell surface receptor and a peptide subunit of an α-helical coiled-coil. More specifically, the invention relates to fusion proteins comprised of a cytoplasmic domain of a receptor and a peptide subunit of an α-helical coiled-coil, and to homodimers and heterodimers of such fusion proteins. The invention also specifically relates to fusion proteins comprised of a protein of an ectodomain of a transforming growth factor β membrane-bound receptor and a peptide subunit of an α-helical coiled-coil, and to homodimers and heterodimers of such fusion proteins.

BACKGROUND OF THE INVENTION

The biological activity of proteins often depends on conformation, where a certain tertiary or quaternary structure is needed for activity. Expression of recombinant proteins in a biologically-active conformation, for use as a therapeutic agent or in screening and diagnostic methods, is a significant technical challenge.

One approach to preparing soluble forms of the extracellular domain of transmembrane proteins is to delete the transmembrane and intracytoplasmic domains while retaining or adding an appropriate signal peptide to enable secretion of the soluble form of the protein (Smith et al., Science, 238:1704 (1987); Treiger et al., J. Immunol. 136:4099 (1986)). Another approach is to express the soluble protein as a fusion protein by joining the extracellular domain of the protein to an immunoglobulin heavy chain constant region (Fanslow et al., J. Immunol. 149:65 (1992)). However, these approaches often do not achieve, or permit the attainment of, the proper tertiary or quaternary structure required for maximal biological activity. Even if the protein is active, it may be poorly expressed or unstable. Thus, there remains a need in the art to prepare recombinant proteins that are biologically active and stable.

One set of proteins of particular interest are mature transforming growth factor-β (TGF-β) and corresponding receptors, which are involved in normal physiological processes including the regulation of cell growth, differentiation, and immune responses. TGF-β mediates signaling by binding to and complexing three types of cell surface receptors known as the TGF-β type I (TβRI), type II (TβRII) and type III (TβRIII) receptors (Massague, J., Annu. Rev. Biochem. 67:753-791 (1998)). In the absence of ligand, both the type I and the type II receptors can form homodimers (Gilboa, L., et al., J. Cell Biol. 140:767-777 (1998)). However, these ligand-independent receptor dimers are not active due to a negative regulatory effect exerted by their extracellular domains (Zhu, H. J. and Sizeland, A. M., J. Biol. Chem. 274:29220-29227 (1999)). At least three TGF-β isoforms (TGF-β1, -β2 and -β3) are present in mammalian cells. The TGF-β1 and TGF-β3 ligand isoforms, which have a high affinity for the type II receptor extracellular domain, promote the formation of a signaling competent complex by simultaneously binding to two type II receptor extracellular domains (Letourneur, O. et al., Biochem. Biophys. Res. Commun. 224:709-716 (1996); Hart, P. J. et al., Nat. Struct. Biol. 9:203-208 (2002)). This binding event is thought to re-orient the type II receptors at the cell surface (Zhu, H. J. and Sizeland, A. M., J. Biol. Chem. 274:11773-11781 (1999)), allowing for the recruitment of two type I receptors in a signaling competent manner (Yamashita, H. et al., J. Biol. Chem. 269:20172-20178 (1994)). The type II receptor kinases can then transphosphorylate the cytoplasmic domains of the type I receptor within the complex. The signal is then translocated to the nucleus by a cascade of events involving primarily members of the Smad family (Attisano, L. and Wrana, J. L., Cytokine Growth Factor Rev. 7:327-339 (1996); Attisano, L. and Wrana, J. L., Curr. Opin. Cell Biol. 10:188-194 (1998); Massague, J., Nat. Rev. Mol. Cell Biol. 1:169-178 (2000)).

TβRIII is generally thought to be an 'accessory' receptor whose role is to present ligand to the signaling receptors (Lopez-Casillas, F. et al., Cell 73:1435-1444 (1993)). The idea that there is a need for this type of 'accessory' receptor is supported by the fact that the affinity of the TGF-β2 isoform for TβRII is low relative to the other mammalian isoforms (Cheifetz, S. et al., Cell 48:409-415 (1987); Cheifetz, S., et al. J. Biol. Chem. 265:20533-20538 (1990); Segarini, P. R. et al., Mol. Endocrinol. 3:261-272 (1989)). Recent studies suggest, however, that the role of TβRIII is more complex since TβRIII is required for both TGF-β1 or -β2 promoted mesenchymal transformation during chick embryonic heart development (Brown, C. B. et al., Science 283:2080-2082 (1999)). Also, it has been shown that the TβRIII cytoplasmic domain can be phosphorylated by, and interact with, TβRII and that this interaction is necessary for the promotion of signaling (Blobe, G. C. et al., J. Biol. Chem. 276:24627-24637 (2001)). In contrast, in other cell types, TβRIII inhibits TGF-β signaling by preventing TβRI-TβRII complex formation (Eickelberg, O. et al., J. Biol. Chem. 277:823-829 (2002)). TβRIII is found at the cell surface in a form containing glycosaminoglycan sulfate chains, which makes it electrophoretically heterogeneous (Lopez-Casillas, F. et al., Cell 67:785-795 (1991)). Two independent TGF-β binding domains were identified within the TβRIII ectodomain by mutational analysis (Fukushima, D. et al., J. Biol. Chem. 268:22710-22715 (1993); Pepin, M. C. et al., Proc. Natl. Acad. Sci. U.S.A, 91:6997-7001 (1994)). In agreement with this, the soluble ectodomain of TβRIII was shown to be able to bind to two TGF-β molecules simultaneously (De Crescenzo, G. et al., J. Biol. Chem. 276:29632-29643 (2001)).

TGF-β overexpression has been shown to play a key role in several human disorders including fibrotic diseases which are characterized by an abnormal accumulation of extracellular matrix (Border, W. A. and Noble, N. A., Am. J. Kidney Dis. 22:105-113 (1993)). It also plays a role in cancer, where TGF-β appears to play a significant role as a tumor suppressor since mutations or deletions in the genes for Smad signaling proteins and TβRII are observed in human tumors (Massague, J. et al., Cell 103:295-309 (2000)). On the other hand, there is strong evidence that, in the later stages of tumor progression, TGF-β promotes metastasis (Wakefield, L. M. and Roberts, A. B., Curr. Opin. Genet. Dev. 12:22-29 (2002)). Accordingly, it would be desirable to provide TGF-β receptors, or domains of these receptors, in their biologically-active form suitable for use as a therapeutic agent, or for use in screening and diagnostic assays. More generally, it would be desirable to provide a receptor domain of any selected protein in soluble form and in a biologically active conformation for use as a therapeutic agent and for use in various screening and diagnostic assays, and preferably in a cell free assay.

SUMMARY OF THE INVENTION

In one aspect, the invention provides a fusion protein, comprising all or a portion of an extracellular domain of a cell surface receptor for transforming growth factor-β and a peptide subunit of an α-helical coiled-coil.

The fusion protein, in one embodiment, contains a K coil or an E coil peptide subunit having between 3-10 heptad repeat units. The heptad repeat, in another embodiment, has a sequence selected from the group of sequences identified as SEQ ID NOs:11-17. In preferred embodiments, the peptide subunit has a sequence identified herein as SEQ ID NO:8 (K5) or as SEQ ID NO:5 (E5).

In another embodiment, the extracellular domain is from a cell surface receptor selected from the group consisting of receptors for transforming growth factor-β type II and transforming growth factor-β type III.

The fusion protein, in some embodiments, is bound to a second fusion protein to form a coiled-coil dimer where the second fusion protein is comprised of an extracellular domain of a transforming growth factor-β receptor and a second peptide subunit of the α-helical coiled-coil.

In another aspect, the invention includes a polynucleotide comprising a nucleotide sequence encoding the fusion protein described above.

In yet another aspect, the invention contemplates a vector comprising the polynucleotide encoding for the fusion protein.

In still another aspect, the invention includes a coiled-coil dimer protein, comprised of (1) a first extracellular domain of all or a portion of a cell surface receptor for transforming growth factory and a first peptide subunit of an α-helical coiled-coil, and (2) either (i) the first extracellular domain and a second peptide subunit of the α-helical coiled-coil, or (ii) a second extracellular domain of all or a portion of a cell surface receptor for transforming growth factor-β and a second peptide subunit of the α-helical coiled-coil.

In one embodiment the coiled-coil protein is a homodimer by virtue of being comprised of a first extracellular domain joined to the first and the second peptide subunits. In another embodiment, the coiled-coil protein is a heterodimer by virtue of being comprised of a first extracellular domain and of a second extracellular domain joined respectively to first and second peptide subunits, the first and second extracellular domains being different.

In another embodiment, the extracellular domain is a cell surface receptor selected from the group consisting of transforming growth factor-β type II receptor and transforming growth factor-β type III receptor.

The first peptide subunit of the α-helical coiled-coil, in another embodiment, has a sequence identified herein as SEQ ID NO:8 (K5). The second peptide subunit of the α-helical coiled-coil can have a sequence identified herein as SEQ ID NO:5 (E5).

In another aspect, the invention includes the use of the fusion protein described above as a biopharmaceutical agent for treatment of a condition characterized by TGF-β binding to a TGF-β receptor.

In another aspect, the invention also includes a method for selecting a compound capable of inhibiting binding activity. The method is comprised of preparing a coiled-coil protein comprised of (i) all or a portion of an extracellular domain of a TGF-β receptor and a first peptide subunit of an α-helical coiled-coil; and (ii) an extracellular domain of (a) the same TGF-β receptor or of (b) a different TGF-β receptor and a second peptide subunit of the α-helical coiled-coil; incubating the coiled-coil protein with a test compound in the presence of a ligand for the first or second receptor extracellular domain; and measuring the ability of the test compound to inhibit interaction between the ligand and the coiled-coil protein.

In one embodiment, the method includes preparing a coiled-coil protein comprised of an extracellular domain of a transforming growth factor-β receptor selected from the group consisting of transforming growth factor-β type II and transforming growth factor-β type III.

In another embodiment, the method includes preparing a coiled-coil protein comprised of an extracellular domain of a transforming growth factor-β receptor type II joined to the first peptide subunit and the second peptide subunit of the α-helical coiled-coil, to form a coiled-coil homodimer.

In still another embodiment, the method includes preparing a coiled-coil protein comprised of an extracellular domain of a transforming growth factor-β receptor type II and of an extracellular domain of a transforming growth factor-β receptor type III to form a coiled-coil heterodimer.

In the method, the measuring step can include measuring by a competitive binding assay or by surface plasmon resonance.

In yet another aspect of the invention, a method for treating a condition characterized by an overexpression of TGF-β is provided. The method comprises administering a coiled-coil protein capable of inhibiting TGF-β signaling, where the coiled-coil protein is comprised of (i) an extracellular domain of a TGF-β receptor and a first peptide subunit of an α-helical coiled-coil; and (ii) an extracellular domain of (a) the same TGF-β receptor or (b) a different TGF-β receptor, and a second peptide subunit of the α-helical coiled-coil.

Conditions to be treated by the method include, but are not limited to a tissue fibroproliferative disorder, progressive glomerular disease of the kidney, acute respiratory distress syndrome, cirrhosis of the liver, diabetic nephropathy, human mesangial proliferative glomerulonephritis, or tumor metastasis.

The invention also includes, in another aspect, a fusion protein comprising a cytoplasmic domain derived from a cell surface receptor for transforming growth factor-β and a peptide subunit of an α-helical coiled-coil.

The peptide subunit of the fusion protein is selected from K5 and E5. For example, the peptide subunit can have a sequence identified herein as SEQ ID NO:8 (K5) or as SEQ ID NO:5 (E5).

In the fusion protein, the receptor is selected from the group consisting of transforming growth factor-β type I and transforming growth factor-β type II. In one embodiment, the fusion protein is bound to a second fusion protein to form a coiled-coil dimer, the second fusion protein comprised of an cytoplasmic domain of a transforming growth factor-β membrane-bound receptor and a second peptide subunit of the α-helical coiled-coil.

The invention, in another aspect, includes a polynucleotide comprising a nucleotide sequence encoding the fusion protein as well as a vector comprising the polynucleotide.

Also contemplated is a coiled-coil dimer protein, comprising all or a portion of a first cytoplasmic domain of a cell surface receptor for transforming growth factor-β and a first peptide subunit of an α-helical coiled-coil, and (i) the first cytoplasmic domain and a second peptide subunit of the α-helical coiled-coil or (ii) a second cytoplasmic domain derived from a cell surface receptor for transforming growth factor-β, and a second peptide subunit of the α-helical coiled-coil.

In one embodiment, the coiled-coil protein is a homodimer by virtue of being comprised of a first cytoplasmic domain joined to the first and second peptide subunits. In another embodiment, the coiled-coil protein is a heterodimer by virtue of being comprised of first and second cytoplasmic domains, which are different, joined to the first and the second peptide subunits, respectively.

In various embodiments, the receptor in the coiled-coil protein is selected from the group consisting of transforming growth factor-β type I and transforming growth factor-β type II. The first peptide subunit of the α-helical coiled-coil has a sequence identified herein as SEQ ID NO:8 (K5), in one embodiment. The second peptide subunit of the α-helical coiled-coil has a sequence identified herein as SEQ ID NO:5 (E5), in one embodiment.

In yet another aspect, the invention provides a method for selecting a compound capable of inhibiting kinase activity. The method involves preparing a coiled-coil protein comprised of (i) a cytoplasmic domain of a TGF-β receptor and a first peptide subunit of an α-helical coiled-coil; and (ii) a cytoplasmic domain of (a) the same TGF-β receptor or (b) a different TGF-β receptor, and a second peptide subunit of the α-helical coiled-coil. The coiled-coil protein is incubated with a test compound; and the ability of the test compound to inhibit receptor cross phosphorylation is determined, as measured by a suitable technique for detecting the level of phosphorylation, such as $^{33}$P-ATP or mass spectrometry.

In one embodiment, the method includes preparing a coiled-coil protein comprised of a cytoplasmic domain of a transforming growth factor-β receptor selected from the group consisting of transforming growth factor-β type I and transforming growth factor-β type II.

In another embodiment, the method includes preparing a coiled-coil protein comprised of a cytoplasmic domain of a transforming growth factor-β receptor type I joined to the first peptide subunit and to the second peptide subunit of the α-helical coiled-coil, to form a coiled-coil homodimer.

In another embodiment, the method includes preparing a coiled-coil protein comprised of a cytoplasmic domain of a transforming growth factor-β receptor type II joined to the first peptide subunit and to the second peptide subunit of the α-helical coiled-coil, to form a coiled-coil homodimer.

Also contemplated is an embodiment where the coiled-coil protein is comprised of a cytoplasmic domain of a transforming growth factor-β receptor type I and of a cytoplasmic domain of a transforming growth factor-β receptor type II to form a coiled-coil heterodimer.

These and other objects and features of the invention will be more fully appreciated when the following detailed description of the invention is read in conjunction with the accompanying drawings.

BRIEF DESCRIPTION OF THE FIGURES

FIG. 1A shows the amino acid sequence of a fusion protein comprised of an ectodomain of transforming growth factor-β receptor type II (TβRIIED) and an E5 coil (TβRIIED-E5; SEQ ID NO:1), where residues 1 to 26 correspond to residues 1 to 26 of the TβRII sequence (SEQ ID NO:2) according to the numbering used in the Swiss-Protein database (accession number: P37173); TβRIIED-E5 residues 27 to 36 (underlined) correspond to a myc tag (SEQ ID NO: 3); TβRIIED-E5 residues 37 to 170 correspond to residues 27 to 160 of the TβRII sequence in the Swiss-Protein database; residues 171 to 181 (underlined) correspond to an 11 amino-acid linker (SEQ ID NO:4); residues 182 to 216 correspond to the E5 coil (SEQ ID NO:5); and residues 217 to 224 correspond to the His tag (underlined) separated from the E5 coil sequence by two glycines (SEQ ID NO:5).

FIG. 1B shows the amino-acid sequence of a fusion protein comprised of an ectodomain of transforming growth factor-β receptor type II (TβRIIED) and a K5 coil (TβRIIED-K5; SEQ ID NO: 7). Residues 1 to 26 correspond to residues 1 to 26 of the TβRII sequence (SEQ ID NO:2) according to the numbering used in the Swiss-Protein database (accession number: P37173); TβRIIED-K5 residues 27 to 36 (underlined) correspond to a myc tag (SEQ ID NO:3); TβRIIED-K5 residues 37 to 170 correspond to residues 27 to 160 of the TβRII sequence in the Swiss-Protein database; residues 171 to 181 (underlined) correspond to an 11 amino-acid linker (SEQ ID NO:4); residues 182 to 216 correspond to the K5 coil (SEQ ID NO: 3) and residues 217 to 224 correspond to the His tag (underlined) separated from the K5 coil sequence by two glycines (SEQ ID NO:6).

FIG. 1C shows the amino-acid sequence of a fusion protein comprised of the membrane proximal region of the ectodomain of transforming growth factor-β receptor type II (MP-TβRIIED) and an K5 coil (MP-TβRIIED-K5; SEQ ID NO: 9). Residues 1 to 25 correspond to residues 1 to 25 of the rat TβRIII sequence (SEQ ID NO:10) according to the numbering used in the Swiss-Protein database (accession number P26342); MP-TβRIIIED-K5 residues 26 to 35 (underlined) correspond to a myc tag (SEQ ID NO:3); MP-TβRIIIED-K5 residues 36 to 242 correspond to residues 576 to 782 of the rat TβRIII sequence In the Swiss-Protein database; residues 243 to 253 (underlined) correspond to an 11 amino-acid linker (SEQ ID NO:4); residues 254 to 288 correspond to the K5 coil (SEQ ID NO: 3); and residues 291 to 296 correspond to the His tag (underlined) separated from the K5 coil sequence by two glycines (SEQ ID NO:6).

FIGS. 2A-2B show the purification of TβRIIED-E5 fusion protein (SEQ ID NO:1) using standard Ni-NTA affinity chromatography. FIG. 2A shows the Coomassie Blue staining of various fractions collected during the purification of TβRIIED-E5 after resolving the proteins on a 4-12% gradient gel (reducing conditions). Lanes W1 and W2 correspond to the two first buffer A wash steps; Lane FT corresponds to the flow through after the last column loading; Lane 1 corresponds to the 1$^{st}$ elution. FIG. 2B shows the results of Western blotting of various fractions collected during the purification after resolving the proteins on 11% SDS-PAGE (non-reducing conditions) using an anti-myc antibody as the primary antibody, and a horseradish peroxidase conjugated goat anti-mouse antibody as a secondary antibody. Lane 1 corresponds to the 1$^{st}$ elution (the same sample as in Lane 1 of FIG. 2A) and lanes 2 and 3 correspond to the 2$^{nd}$ and 3$^{rd}$ elutions, respectively.

FIGS. 3A-3G show the purification of TβRIIED-K5 (SEQ ID NO:7) and MP-TβRIIIED-K5 (SEQ ID NO: 9). TβRIIED-K5 protein was eluted from a Ni-NTA affinity chromatography column and was run on 11% SDS-PAGE under non-reducing (FIG. 3A) and reducing conditions (FIG. 3B and FIG. 3C) followed by Western blotting (FIG. 3A and FIG. 3B; primary and secondary antibody as in FIG. 2) or silver staining (FIG. 3C). After separation with a Centriprep 30 device, a 10 μL aliquot of monomeric TβRIIED-K5 was run on 11% SDS-PAGE under non-reducing conditions (FIG. 3D), 10 μL of a 1/15 dilution of the sample shown in Lane A was also run for comparison (FIG. 3E). MP-TβRIIIED-K5 protein eluted from a NI-NTA affinity chromatography column was run on 11% SDS-PAGE under non-reducing conditions, followed by Western blotting (primary antibody: anti-myc; secondary antibody: horseradish peroxidase conjugated goat anti-mouse; FIG. 3F) and by silver staining (FIG. 3G).

In FIG. 4A, MP-TβRIIED-K5 (SEQ ID NO:9) was injected over the anti TGF-βRII antibody-loaded biosensor surface ("1") and a control surface, followed by a TβRIIED-E5 (SEQ ID NO:1) Injection ("2") and another MP-TβRIIED-K5 ("3"). In FIG. 4B, untagged hTβRII ED was injected over the anti-TGF-βRII antibody-loaded biosensor surface and over a control surface ("1"), followed by injection of MP-TβRII-IED-K5 ("2"). In FIG. 4C five concentrations of TβRII ED-E5 coil solutions were successively injected on the anti-TGF-βRII-loaded biosensor surface and a control surface ("1-5"), followed by injection of TβRII ED-K5 ("6").

FIG. 5A is a global fit of the TβRIIED-K5/TGF-β1 interaction sensorgrams, where different concentrations of TβRI-IED-K5 ranging from 9.9 to 50 nM (in addition to buffer injection) were injected over 250 RUs of coupled TGF-β1 and over a control surface. The points correspond to the resonance units after data preparation and the solid lines represent the fit when globally fitting the data set with a two-to-one stoichiometry model. FIG. 5B shows the residuals from the global fit of the TβRIIED-K5/TGF-β1 interaction with the two-to-one stoichiometry model. FIG. 5C shows the residuals from the global fit of the TβRIIED-K5/TGF-β1 interaction with a simple one-to-one model. FIG. 5D is a global fit of the sensorgrams of the interaction of TβRIIED-K5/TβRIIED-E5 with TGF-β1, where different concentrations of TβRIIED-K5, preincubated with the same amount of TβRIIED-E5, ranging from 9.9 to 50 nM were injected over the same TGF-β1 surface and over a control surface. The points are the resonance units obtained after data preparation and the solid lines represent the fit when globally fitting the data set with a rearrangement model. FIG. 5E shows the residuals from the global fit of the sensorgrams of the interaction of TβRIIED-K5/TβRIIED-E5 with TGF-β1 with the rearrangement model. FIG. 5F shows the residuals from the global fit of the TβRIIED-K5/TβRIIED-E5 interaction with TGF-β1 with the avidity model.

FIG. 6A shows the arbitrary resonance units (RUs) as a function of time for different concentrations of MP-TβRIIED-K5 (SEQ ID NO:9). FIGS. 6B-6C show the residuals from the global fit of the MP-TβRIIED-K5 coil/TGF-β1 interaction with the rearrangement model (FIG. 6B) and the simple one-to-one model (FIG. 6C). FIG. 6D shows the RUs as a function of time for different concentrations of MP-TβRIIIED-K5 preincubated with the same amount of TβRIIED-E5.

FIG. 10A shows the amino acid sequence of the erbB1CD-K5 fusion protein (SEQ ID NO:31). erbB1CD-K5 residues 1 to 6 (underlined) correspond to a 6 amino-acid linker (SEQ ID NO:32); erbB1CD-K5 residues 7 to 41 correspond to the K5 coil (SEQ ID NO:8); erbB1 CD-K5 residues 42 to 48 (underlined) correspond to 7 amino-acid linker (SEQ ID NO:33); erbB1CD-K5 residues 49 to 590 correspond to residues 669 to 1210 comprising the cytoplasmic domain of the human erbB1 sequence according to the numbering used in the Swiss Protein database (accession number: P00533); erbB1CD-K5 residues 591 to 596 (underlined) correspond to a 6 amino-acid His tag peptide sequence.

FIG. 10B shows the amino acid sequence of the erbB1 cytoplasmic domain—E5 (erbB1Cd-E5) fusion protein (SEQ ID NO:34). erbB1CD-E5 residues 1 to 6 (underlined) correspond to a 6 amino-acid linker (SEQ ID NO:32); erbB1CD-E5 residues 7 to 41 correspond to the E5 coil (SEQ ID NO:5); erbB1CD-E5 residues 42 to 48 (underlined) correspond to 7 amino-acid linker (SEQ ID NO:33); erbB1 CD-E5 residues 49 to 590 correspond to residues 669 to 1210 comprising the cytoplasmic domain of the human erbB1 sequence according to the numbering used in the Swiss Protein database (accession number: P00533); erbB1CD-E5 residues 591 to 596 (underlined) correspond to a 6 amino-acid His tag peptide sequence.

BRIEF DESCRIPTION OF THE SEQUENCES

Figure 4A:
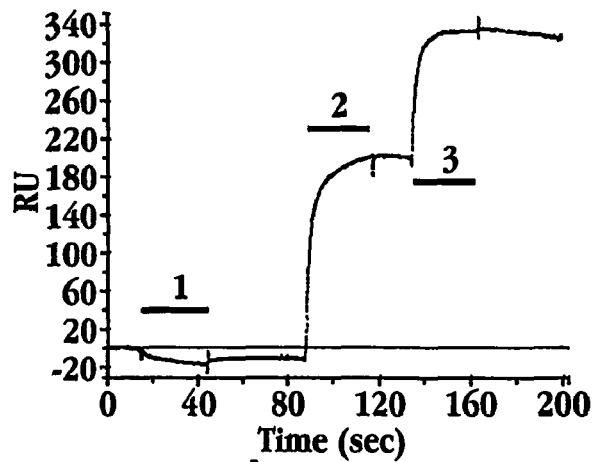
FIGS. 4A-4C are sensorgrams generated from a surface plasmon resonance (SPR) biosensor study showing dimerization, in arbitrary resonance units (RU), as a function of time.

SEQ ID NO:1 is the amino acid sequence of the fusion protein shown in FIG. 1A, which is comprised of the myc tagged extracellular domain of TGF-β receptor II (TβRIIED, SEQ ID NO:2) joined by a linker (SEQ ID NO:4) to a E coil subunit (SEQ ID NO:5) and a C-terminal His tag plus two glycines (SEQ ID NO:6).

SEQ ID NO:2 is the amino acid sequence of the extracellular domain of TGF-β receptor II, including a myc tag sequence (underlined, SEQ ID NO:3).

SEQ ID NO:3 is the amino acid sequence of the myc tag included in SEQ ID No. 1, 7, and 9.

SEQ ID NO:4 is the amino acid sequence of the linker between the extracellular domain of TGF-β receptor II and the coiled-coil subunit.

SEQ ID NO:5 is the amino acid sequence of an E coil subunit of a coiled-coil heterodimer, formed of five heptad repeat units.

SEQ ID NO:6 is the amino acid sequence of the histidine tag plus two glycines.

SEQ ID NO:7 is the amino acid sequence of the fusion protein shown in FIG. 1B, comprised of the myc tagged extracellular domain of TGF-β receptor II (TβRIIED, SEQ ID NO:2) joined by a linker (SEQ ID NO:4) to a K coil subunit (SEQ ID NO:8) and a C-terminal His tag plus two glycines (SEQ ID NO:6).

SEQ ID NO:8 is the amino acid sequence of a K coil subunit of the coiled-coil heterodimer, formed of five heptad repeat units.

SEQ ID NO:9 is the amino acid sequence of the fusion protein shown in FIG. 1C, comprised of the myc tagged membrane proximal domain of the extracellular domain of TGF-β receptor III (SEQ ID NO:10) joined by a linker (SEQ ID NO:4) to a K coil subunit (SEQ ID NO:8) and a C-terminal His tag plus two glycines (SEQ ID NO:6).

SEQ ID NO:10 is the amino acid sequence of the membrane proximal domain of the extracellular domain of TGF-β receptor III (MP-TβRIIIED), including a myc tag (underlined).

SEQ ID NO:11 is the amino acid sequence of the heptad repeat used in the E coil subunit of SEQ ID NO:5.

SEQ ID NO:12 is an amino acid sequence of a heptad repeat for use in an E coil subunit of a coiled-coil dimer.

SEQ ID NO:13 is an amino acid sequence of a heptad repeat for use in an E coil subunit of a coiled-coil dimer.

SEQ ID NO:14 is an amino acid sequence of a heptad repeat for use in an E coil subunit of a coiled-coil dimer.

SEQ ID NO:15 is the amino acid sequence of the heptad repeat used in the K coil subunit of SEQ ID NO:8.

SEQ ID NO:16 is an amino acid sequence of a heptad repeat for use in a K coil subunit of a coiled-coil dimer.

SEQ ID NO:17 is an amino acid sequence of a heptad repeat for use in an E coil subunit of a coiled-coil dimer.

SEQ ID NO:18 is an E coil subunit peptide having 5 heptad units.

SEQ ID NO:19 is a K coil subunit peptide having 5 heptad units.

SEQ ID NO:20 is the amino acid sequence of the K coil subunit of the coiled-coil heterodimer with additional Cys and Gly residues at the N-terminus.

SEQ ID NO:21 is the amino acid sequence of the fusion protein comprised of the cytoplasmic domain of the TGF-β receptor II joined by glycine linkers to an E coil subunit (SEQ ID NO:5)

SEQ ID NO:22 is the amino acid sequence of the fusion protein comprised of the cytoplasmic domain of the rat TGF-β receptor I joined by glycine linkers to a K coil subunit (SEQ ID NO:8).

SEQ ID NO:23 is nucleic acid primer for amplification of the cDNA encoding for K5 coil (SEQ ID NO:8).

SEQ ID NO:24 is nucleic acid primer for amplification of the cDNA encoding for K5 coil (SEQ ID NO:8).

SEQ ID NO:25 is nucleic acid primer for amplification of the cDNA encoding for MP-TβRIIIED.

SEQ ID NO:26 is nucleic acid primer for amplification of the cDNA encoding for MP-TβRIIIED.

SEQ ID NO:27 is nucleic acid primer for amplification of the cDNA encoding for TGFβ type II receptor kinase domain.

SEQ ID NO:28 is nucleic acid primer for amplification of the cDNA encoding for TGFβ type II receptor kinase domain.

SEQ ID NO:29 is nucleic acid primer for amplification of the cDNA encoding for TGFβ type I receptor kinase domain.

SEQ ID NO:30 is nucleic acid primer for amplification of the cDNA encoding for TGFβ type I receptor kinase domain.

SEQ ID NO:31 is the amino acid sequence of the erbB1CD-K5 fusion protein shown in FIG. 10A and comprised of a 6 amino-acid linker (SEQ ID NO:32); a K5 coil (SEQ ID NO:8); a 7 amino-acid linker (SEQ ID NO:33), and residues 669-1210 of human erbB1 sequence (Accession number: P00533) followed by 6 histidine residues.

SEQ ID NO:32 is the amino acid sequence of a linker at the N-terminus of the cytoplasmic domain of erbB1.

SEQ ID NO:33 the amino acid sequence of a linker between the coiled-coil subunit and the cytoplasmic domain of erbB1.

SEQ ID NO:34 is the amino acid sequence of the erbB1CD-E5 fusion protein shown in FIG. 10B and comprised of a 6 amino-acid linker (SEQ ID NO:32); an E5 coil (SEQ ID NO:5); a 7 amino-acid linker (SEQ ID NO:33), and residues 669-1210 of human erbB1 sequence (Accession number: P00533) followed by 6 histidine residues.

SEQ ID NO:35 is the nucleic acid primer to amplify cDNA encoding erbB1 cytoplasmic domain.

SEQ ID NO:36 is the nucleic acid primer used to amplify cDNA encoding erbB1 cytoplasmic domain with attached C-terminal 6×His tag sequence.

SEQ ID NO:37 is the nucleic acid primer used to amplify cDNA encoding erbB1 cytoplasmic domains.

DETAILED DESCRIPTION OF THE INVENTION

I. Definitions and Abbreviations

Unless otherwise indicated, all terms herein have the same meaning as they would to one skilled in the art of the present invention. Practitioners are particularly directed to *Current Protocols in Molecular Biology* (Ausubel, F. M. et al., John Wiley and Sons, Inc., Media Pa.) for definitions and terms of the art.

Abbreviations for amino acid residues are the standard 3-letter and/or 1-letter codes used in the art to refer to one of the 20 common L-amino acids.

"Peptide" and "polypeptide" are used interchangeably herein and refer to a compound made up of a chain of amino acid residues linked by peptide bonds. Unless otherwise indicated, the sequence for peptides is given in the order from the amino terminus to the carboxyl terminus.

The terms "extracellular domain" and "ectodomain" are used interchangeably and are abbreviated "ED."

The terms "cytoplasmic domain" and "kinase domain" are used interchangeably.

"TβRIIED" refers to the extracellular domain of the cell surface TGF-β type II receptor.

"MP-TβRIIIED" refers to the membrane-proximal domain (i.e., C-terminal) of TGF-β type III receptor ectodomain.

EGFR refers to a receptor for epidermal growth factor, including erbB1, erbB2, erbB3, erbB4.

SPR refers to surface plasmon resonance.

RU refers to resonance unit.

II. Ectodomain Fusion Protein Preparation and Characterization

In a first aspect, the invention relates to a fusion protein comprised of an ectodomain of a membrane-bound receptor attached to a peptide subunit of an α-helical coiled-coil. In this section, preparation and characterization of exemplary fusion proteins using as models two ectodomains from TGF-β receptors are described. Specifically, the first model is a fusion protein comprised of the ectodomain from the TGF-β type II receptor (TβRIIED) and a K5 coil or an E5 coil of an E5/K5 coiled-coil. The second model is a fusion protein comprised of the membrane-proximal domain (i.e., C-terminal) of the TGF-β type III receptor ectodomain (MP-TβRIIIED) fused to a K5 coil. These fusion proteins were characterized in terms of kinetics of binding to TGF-β1 using a surface plasmon resonance (SPR)-based biosensor. The ability of the fusion proteins tagged with an E5 coil to dimerize with a fusion protein tagged with a K5 coil was studied, and is described below. Binding of the coiled-coil induced homodimeric and heterodimeric receptor ectodomains to TGF-β1 and their ability to inhibit TGF-β1 signaling in vitro was studied, and is described below.

A. Preparation and Expression of Fusion Proteins

FIGS. 1A-1C show the amino acid sequences of the exemplary fusion proteins designed and expressed for the invention described herein. FIG. 1A shows a fusion protein referred to as TβRIIED-E5 and identified herein as SEQ ID NO:1. This fusion protein is comprised of the myc-tagged extracellular domain of TGF-β receptor type II (SEQ ID NO:2) joined via a linker (SEQ ID NO:4) to an E coil formed of five heptad repeat units (SEQ ID NO:5; amino acid residues 182-216 of the sequence in FIG. 1A) of a coiled-coil dimer, described below.

FIG. 1B shows a second exemplary fusion protein, referred to herein as TβRIIED-K5 and identified as SEQ ID NO:7. This fusion protein is comprised of the myc-tagged extracellular domain of TGF-β receptor type II (SEQ ID NO:2) joined via a linker (SEQ ID NO:4) to a K coil formed of five heptad repeat units (SEQ ID NO:8) of a coiled-coil dimer.

FIG. 1C shows a third exemplary fusion protein referred to herein as MP-TβRIIIED-K5 and identified as SEQ ID NO:9. MP-TβRIIIED is comprised of the myc-tagged membrane proximal domain of the extracellular domain of TGF-β receptor type III (SEQ ID NO:10) joined via a linker (SEQ ID NO:4) to a K coil (SEQ ID NO:8) of a coiled-coil dimer.

The three exemplary fusion proteins shown in FIGS. 1A-1C were N-terminally myc-tagged (SEQ ID NO:3) for detection, and C-terminally His tagged (SEQ ID NO:6) for purification.

The coiled-coil peptides used in construction of the fusion proteins and the peptide dimers described herein are comprised of a first coil-forming peptide, also referred to herein as a first peptide subunit, and second coil-forming peptide, also referred to herein as a second peptide subunit. The two coils assemble into a heterodimer coiled-coil (coiled-coil heterodimer) in either parallel or antiparallel configurations. In a parallel configuration, the two heterodimer-subunit peptide helices are aligned such that they have the same orientation (amino-terminal to carboxyl terminal). In an anti-parallel configuration, the two heterodimer-subunit peptide helices are arranged such that the amino-terminal end of one helix is aligned with the carboxyl-terminal end of the other helix, and vice versa. Exemplary heterodimer subunits are described in PCT patent application WO 95/31480 entitled "Heterodimer Polypeptide Immunogen Carrier Composition and Method", publication date 23 Nov. 1995, which is incorporated herein by reference in its entirety. Heterodimer-subunit peptides designed in accordance with the guidance presented in WO 95/31480 typically show a preference for assembling in a parallel orientation versus an antiparallel orientation.

The first and second peptide subunits of the coiled-coil heterodimer are also referred to herein as a "K-coil" ("K"), referring to positively charged subunits, whose charge is provided dominantly by lysine residues, and an E-coil ("E"), referring to negatively charged subunits whose charge is provided dominantly by glutamic acid residues. The K coil and the E coil are typically comprised of seven amino acid residues, referred to as a heptad unit, that is repeated a selected number of times. The peptide subunits of the coiled-coil peptide are generally of similar size, and typically are the same size, each ranging from about 21 to about 70 residues (3-10 heptads) in length. Exemplary SEQ ID NO:5 is comprised of 5 heptad repeats, hence is referred to herein as "E5." However, it will be appreciated that fewer or more repeats can be used. Similarly, SEQ ID NO:8, the K coil subunit, is comprised of five heptad repeats, and is referred to herein as "K5", however 3-10 heptad units are considered suitable for formation of the coil.

The seven residues forming the heptad unit for formation of the K coil and the E coil can vary. The heptad unit for formation of the E5 coil identified as SEQ ID NO:5 is comprised of the following amino acid residues: EVSALEK (SEQ ID NO:11). Other heptad units for the E coil include EVSALEC (SEQ ID NO:12), EVSALEK (SEQ ID NO:13), EVEALQK (SEQ ID NO:14). With respect to the K coil, exemplary heptad units include KVSALKE (SEQ ID NO:15), KVSALKC (SEQ ID NO:16), and KVEALKK (SEQ ID NO:17). In constructing an E coil or a K coil subunit, a single heptad unit can be repeated to form a subunit of a desired length. For example, the E5 coil subunit identified as SEQ ID NO:5 is based on the heptad unit EVSALEK (SEQ ID NO:11) repeated five times. An E coil or a K coil can also be constructed from two or more different heptad units to obtain a coil of a desired length. For example, an E5 coil subunit comprised of the heptad units identified as SEQ ID NOS:11, 12, and 14 is identified herein as SEQ ID NO:18. In SEQ ID NO:18, the two terminal heptad units have the sequence represented as SEQ ID NO:14, and the three intermediate heptad units have the sequences represented by SEQ ID NO:11 and SEQ ID NO:12. By way of another example, SEQ ID NO:19 corresponds to a K5 coil subunit, where the 5 heptad units are arranged so that the two terminal heptad units are represented as SEQ ID NO:17, with the intermediate units having sequences represented by SEQ ID NO:15 and SEQ ID NO:16. The sequence represented by SEQ ID NO:16 includes a cysteine coupling residue.

Returning now to the fusion proteins shown in FIGS. 1A-1C, construction of pTT2 expression vectors encoding for TβRIIED-E5 (SEQ ID NO:1), TβRIIED-K5 (SEQ ID NO:7), and MP-TβRIIIED-K5 (SEQ ID NO:9) is described in Example 1. The proteins were expressed by transiently transfected HEK 293SF cells using polyethylenimine (PEI) as a transfected vehicle. The fusion proteins were purified from the cell culture medium by affinity column chromatography, also as described in Example 1.

Silver staining or Coomassie Blue staining, and Western blots of SDS-PAGE for the fusion proteins are shown in FIGS. 2A-2B and FIGS. 3A-3G. FIGS. 2A-2B show the purification of TβRIIED-E5 protein by standard Ni-NTA affinity chromatography. FIG. 2A shows the Coomassie Blue staining of various fractions collected during purification of TβRIIED-E5 after resolving the proteins on a 4-12% gradient gel (reducing conditions). Lanes W1 and W2 correspond to two wash steps; Lane FT corresponds to the flow through, Lane 1 corresponds to the elution with imidazole.

FIG. 2B shows Western blotting of various fractions collected during purification after resolving the proteins on 11% SDS-PAGE (non-reducing conditions) using an anti-myc antibody as primary antibody and horseradish peroxidase conjugated goat anti-mouse antibody as a secondary antibody. Lane 1 corresponds to the imidazole elution shown in lane 1 of FIG. 2A. Lanes 2 and 3 correspond to two other imidazole elutions from similar purifications.

FIGS. 3A-3G show the purification of TβRIIED-K5 and MP-TβRIIIED-K5. In the case of TβRIIED-K5 purification, protein eluted from a Ni-NTA affinity chromatography column was run on 11% SDS-PAGE under non-reducing (FIG. 3A) and reducing conditions (FIG. 3B and FIG. 3C) followed by Western blotting (FIG. 3A and FIG. 3B; primary and secondary antibody as in FIG. 2) or silver staining (FIG. 3C). After separation with a Centriprep 30 device to remove disulphide-bridged aggregates, a 10 µL aliquot of monomeric TβRIIED-K5 was run on 11% SDS-PAGE under non-reducing conditions and Western blotted (FIG. 3D). A 10 µL aliquot of a 1/15 dilution of the sample shown in Lane A was also run for comparison (FIG. 3E). In the case of MP-TβRIIIED-K5 purification, protein eluted from a Ni-NTA affinity chromatography column was run on 11% SDS-PAGE under non-reducing condition, followed by Western blotting (primary antibody: anti-myc, FIG. 3F) and by Silver staining (FIG. 3G).

B. Homodimer and Heterodimer Formation

In another study, the ability of the coil tag to mediate dimerization of the TGF-β receptor extracellular domains was demonstrated by using a surface plasmon resonance (SPR)-based biosensor (BIACORE™). This biosensor allows the real-time monitoring of interactions between a surface-immobilized protein (the ligand) and its binding partner (the analyte), which is injected over the surface. As the injection procedes (the wash-on phase), the mass accumulation of the analyte, as It binds to the ligand, is recorded in arbitrary resonance units (RU). The analyte solution is then replaced by buffer and the dissociation of the surface complexes is recorded (the wash-off phase). If needed, the surface is regenerated, i.e. the analyte remaining at the biosensor surface is eluted. This series of steps constitutes a sensorgram.

Example 2 describes the studies performed using the TβRIIED-K5 (SEQ ID NO:7) and the MP-TβRIIIED-K5 (SEQ ID NO:9) fusion proteins discussed above. The fusion proteins were dimerized with a TβRIIED-E5 fusion protein (SEQ ID NO:1) to form a TβRIIED-K5/TβRIIED-E5 dimer and a MP-TβRIIIED-K5/TβRIIED-E5 dimer, through coiled-coil interaction of the K5 and E5 coil tags. An antibody, anti-TGF-β RII, which binds to the extracellular domain of TβRII was coupled to the biosensor surface. In a first study, shown in FIG. 4A, designed to demonstrate that TβRIIED-E5 and MP-TβRIIIED-K5 heterodimerize, the following series of injections was performed. Initially, MP-TβRIIIED-K5 was injected on the antibody surface to evaluate if there was any non-specific binding of MP-TβRIIIED-K5 to the anti-TβRII antibody (FIG. 4A, "1"). The injection was followed by injection of TβRIIED-E5 (FIG. 4A, "2") and then MP-TβRIIIED-K5 (FIG. 4A, "3"). As seen in FIG. 4A, MP-TβRIIIED-K5 did not interact significantly with the antibody, as expected. However, when 200 RUs of TβRIIED-E5 were captured on the biosensor surface through the antibody/TβRIIED interaction, the injection of MP-TβRIIIED-K5 resulted in a strong increase in the SPR signal (140 RUs), indicating that MP-TβRIIIED-K5 bound to the captured TβRIIED-E5.

Figure 4B:
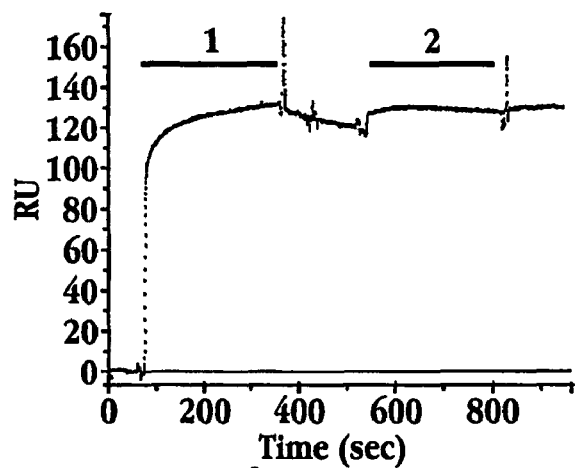

In order to clearly establish that the binding of MP-TβRIIIED-K5 to TβRIIED-E5 was mediated through the coiled-coil interaction, a second study was conducted where an injection of untagged TβRIIED (FIG. 4B, "1") was followed by injection of MP-TβRIIIED-K5 (FIG. 4B, "2"). This study is also described in Example 2. FIG. 4B shows that, in the absence of the E5 tag, TβRIIED was not able to significantly bind to MP-TβRIIIED-K5. Hence the E5 and K5 domains of the TβRIIED-E5 and MP-TβRIIIED-K5 fusion proteins are responsible for the dimerization of the two fusion proteins.

Figure 4C:
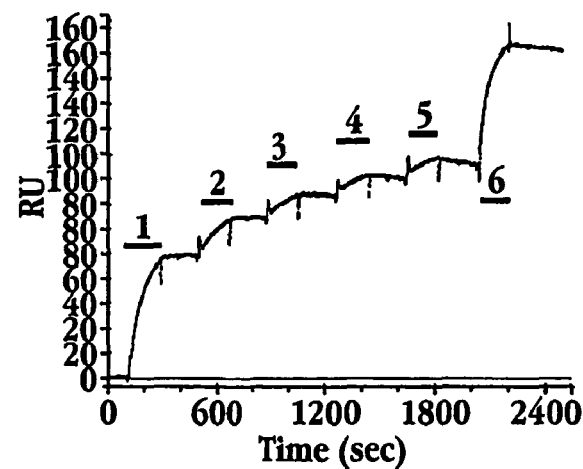

In a third study described in Example 2, the ability of coiled-coil interaction to mediate TβRIIED-E5/TβRIIED-K5 homodimerization was evaluated. Increasing concentrations of TβRIIED-E5 fusion protein (31, 62, 125, 250, 500 nM) were successively injected over the antibody-loaded biosensor surface, and over a control biosensor surface. The results are shown in FIG. 4C and indicate that, after this series of injections, the antibody surface is almost saturated. However, a strong increase in the SPR signal was observed when the TβRIIED-K5 (50 nM) injection followed the TβRIIED-E5 series of injections. This increase is due to a coiled-coil interaction involving the E5 domain of the antibody-captured TβRIIED-E5 and the K5 domain of the injected TβRIIED-K5. This study demonstrates that, as in the case of the MP-TβRIIIED-K5/TβRIIED-E5 interaction, the E5 and K5 coils induced the TβRIIED-K5/TβRIIED-E5 homodimerization.

C. Kinetic Analysis

The binding kinetics of the monomeric forms of the fusion proteins TβRIIED-K5 and MP-TβRIIIED-K5 to TGF-β1 were studied using a BIACORE™ biosensor. Using the same methodology, the binding kinetics of coiled-coil induced TβRIIED-K5/TβRIIED-E5 and MP-TβRIIIED-K5/TβRIIED-E5 dimers were also studied.

1. Binding of TβRIIED-K5 to TGF-β1

The binding characteristics of the monomeric TβRIIED-K5 fusion protein (SEQ ID NO: 7) to TGF-β were tested using the BIACORE™ biosensor. As described in Example 3, TGF-β1 was coupled to the biosensor surface (approximately 250 RUs) by a standard amino coupling procedure. TβRIIED-K5 solutions (9.8, 14.8, 22.2, 33.3 and 50 nM) were then randomly injected in duplicate over the TGF-β1 surface and over a control surface (with no TGF-β1). After data preparation by the 'double referencing' method, the set of sensorgrams was globally fit using a kinetic model depicting the presence of two independent TβRIIED binding sites on the TGF-β1 molecule (two-to-one stoichiometry model). This model was selected since it can depict interactions between untagged TβRIIED or E5-tagged TβRIIED and TGF-β-1 (De Crescenzo, G. et al., *J. Mol. Biol.*, 328(5):1173-83 (2003); De Crescenzo, G., et al., *J. Biol. Chem.* 276:29632-29643 (2001)).

Figure 5A:
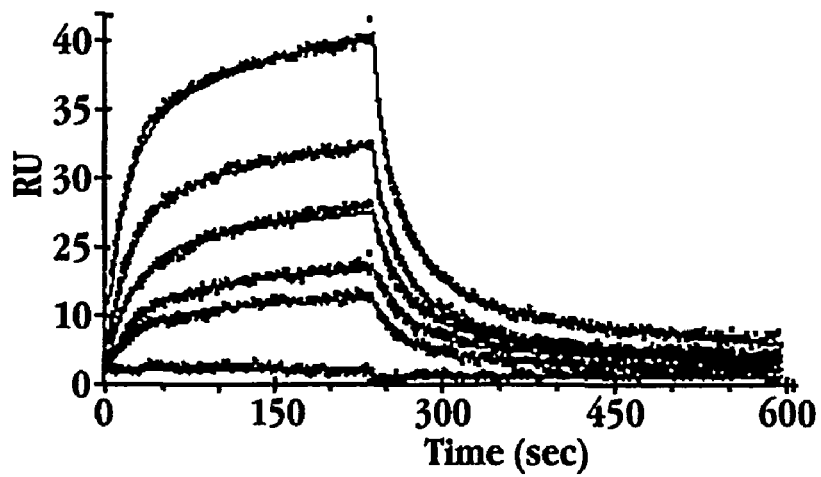
FIGS. 5A-5F show results of kinetic analysis of the TβRI-IED-K5 binding interaction with TGF-β1 (FIGS. 5A-5C) and of the TβRIIED-K5/TβRIIED-E5 binding interaction with TGF-β1 (FIG. 5D-5F). The plots are sensorgrams generated from a surface plasmon resonance biosensor with the TGF-β1 coupled to the sensor surface. The extent of interaction is shown in arbitrary resonance units (RU) as a function of time.
Figure 5B:
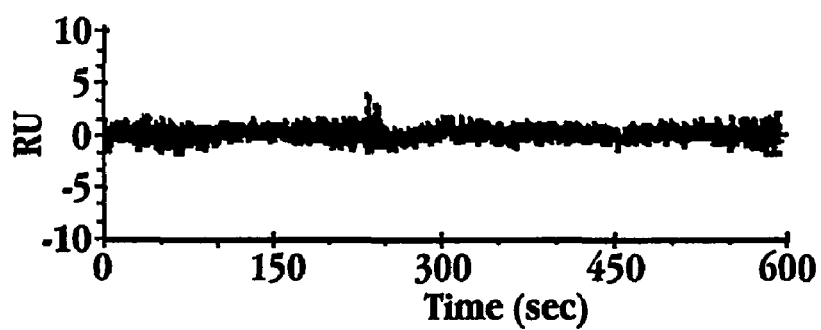
Figure 5C:
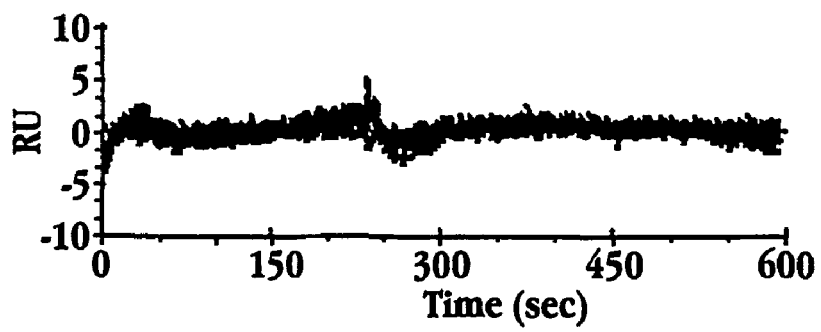

FIG. 5A shows the set of sensorgrams and the fit obtained when using the two-to-one stoichiometry model. For comparison, a simple kinetic model was also used to analyze the data. A better fit was obtained with the two-to-one stoichiometry model as judged by the distribution of the residuals (difference between the experimental and calculated points, FIGS. 5B and 5C). Additionally, as shown in Table 1, the kinetic and thermodynamic constants from the two-to-one stoichiometry model are in good agreement with those previously determined for untagged TβRIIED, indicating that the K5 tag did not influence TβRIIED binding to TGF-β1.

TABLE 1

Kinetic and thermodynamic constants for TGF-β1 (coupled) interacting with TβRIIED-K5 or untagged TβRIIED.

| Kinetic and thermodynamic Parameters | Kinetic Model: Two sites on TGF-β1 | |
|---|---|---|
| | TβRIIED-K5 | TβRIIED** |
| $k_{ass\,1}$ (M$^{-1}$s$^{-1}$) | (3.65 ± 0.2)10$^5$ | (5.4 ± 0.3)10$^5$ |
| $k_{diss\,1}$ (s$^{-1}$) | (3.3 ± 0.7)10$^{-2}$ | (6.5 ± 0.2)10$^{-2}$ |
| $k_{ass\,2}$ (M$^{-1}$s$^{-1}$) | (1.9 ± 0.1)10$^3$ | (1.8 ± 0.1)10$^3$ |
| $k_{diss\,2}$ (s$^{-1}$) | (2.6 ± 0.1)10$^{-3}$ | (1.5 ± 0.3)10$^{-3}$ |
| $K_{d\,1}$ (nM)* | 90 ± 10 (n = 2) | 158 ± 37 (n = 6) |
| $K_{d\,2}$ (nM) | 1250 ± 100 (n = 2) | 981 ± 123 (n = 6) |

*The values given for $K_{d\,1}$ and $K_{d\,2}$ correspond to the average value +/− the standard deviation of n independent experiments.
**from De Crescenzo, G. et al., J. Biol. Chem., 276: 29632–29643 (2001).

2. Binding of Coiled-Coil Induced TβRIIED-K5/TβRIIED-E5 Dimer to TGF-β1

Figure 5D:
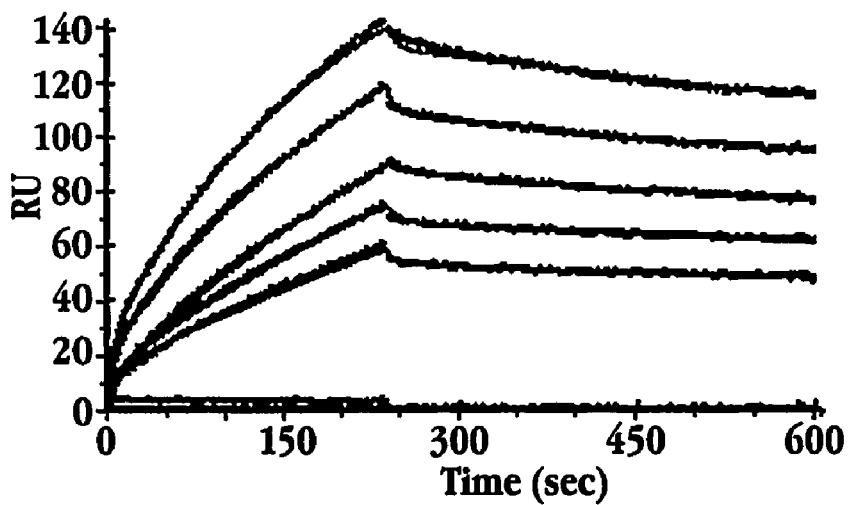

In another study, also described in Example 3, the same TGF-β1 biosensor surface was used to examine the effect of coiled-coil induced dimerization of the TβRIIED. A TβRIIED-K5/TβRIIED-E5 solution that had been incubated at equimolar concentrations (0 to 50 nM) was randomly injected at a flow rate of 50 μL/min in duplicate over the TGF-β1 biosensor surface and over a control surface. FIG. 5D shows the resulting sensorgrams after data preparation. This set of sensorgrams is strikingly different from that corresponding to TβRIIED-K5 injections (compare FIG. 5A and FIG. 5D) in both its wash-on and wash-off phases. This difference in the kinetic behavior of TβRIIED-K5 as compared to the coiled-coil induced TβRIIED-K5/TβRIIED-E5 dimer indicates that dimerization of the coiled-coil domains of the fusion proteins did occur, and that the resulting TβRIIED artificial dimer has a slower apparent off-rate than the monomeric TβRIIED.

The TGF-β1/TβRIIED-K5-TβRIIED-E5 sensorgrams were then globally fit, using different kinetic models. Analysis of the set of sensorgrams with a simple one-to-one model gave poor fits (S.D. of the residuals equal to 6.1, see Table 2). Such a deviation from a simple binding model can be due to the presence of artifacts resulting from non-optimized experimental conditions, such as mass transport limitations or crowding effects (O'Shannessy, D. J. and Winzor, D. J., Anal. Biochem. 236:275-283 (1996)). Alternatively, it can be due to a more complex binding mechanism. In order to verify the absence of mass transport artifacts, the lowest concentration of TβRIIED-K5/TβRIIED-E5 was then injected at 100 μL/min. The resulting sensorgram was superimposable with that performed at 50 μL/min (data not shown), indicating the absence of mass transport limitations. The presence of crowding artifacts is also unlikely since a relatively low amount of coupled TGF-β1 was used, and since it has been previously shown that this artifact is absent when similar TGF-β1 surface densities (De Crescenzo, G. et al., J. Biol. Chem., 276:29632-29643 (2001)).

Having reduced the possibility of artifacts, more complex biological models were then used to fit the data. Since TGF-β1 is a covalent dimer, and since TβRIIED was artificially dimerized through coiled-coil interactions, two scenarios of binding were evaluated. First, the TβRIIED-K5/TβRIIED-E5 dimer can bind to two TGF-β1 molecules at the same time (avidity model) or, second, each TβRIIED domain within the TβRIIED-K5/TβRIIED-E5 dimer binds to one TGF-β1 monomer (such that the dimeric TGF-β bridges the two TβRIIED domains). This results in a sequential binding model where one TβRIIED domain, within the coiled-coil induced dimer, binds to one monomer of TGF-β1, followed by the interaction of the other TβRIIED domain with the other monomer of the same TGF-β1 dimer. This corresponds to an overall one to one (dimer-to-dimer) stoichiometry model with a rearrangement step after the initial binding (rearrangement model). The kinetic and thermodynamic constants from global fitting using these models, in addition to the standard deviation of the residuals and the Z1 and Z2 statistical values, are listed in Table 2.

Figure 5E:
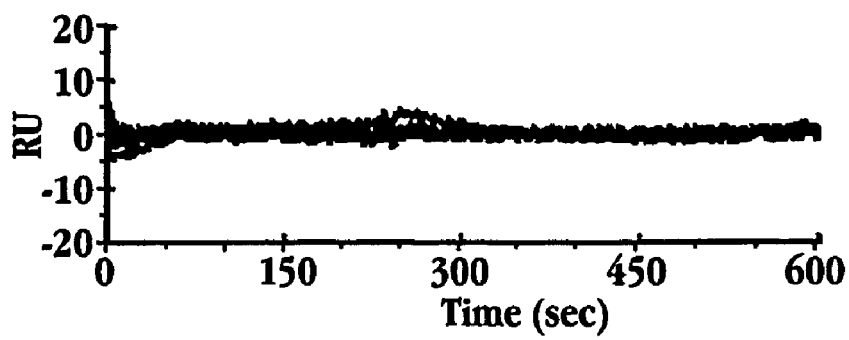
Figure 5F:
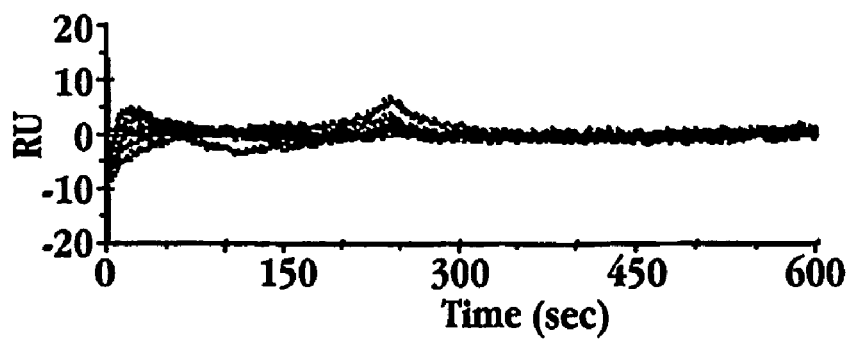

Both complex kinetic models gave better fits than the simple one-to-one model. As shown in FIGS. 5E-5F, the rearrangement model (FIG. 5E) depicted the interaction better than the avidity model (FIG. 5F) since this model exhibited less trend in the residuals. This conclusion was reinforced by the values of the standard deviation of the residuals and the Z1 and Z2 statistics which were lowest in the case of the rearrangement model (Table 2).

TABLE 2

Kinetic and thermodynamic constants for TGF-β1 (coupled) interacting with TβRIIED dimerized through coiled-coil interaction.

| Kinetic and thermodynamic Parameters | TβRIIED dimerized through coiled-coil interaction (simple model) | TβRIIED dimerized through coiled-coil interaction (Avidity model) | TβRIIED dimerized through coiled-coil interaction (Rearrangement model) |
|---|---|---|---|
| $k_{ass\#1}$ (M$^{-1}$s$^{-1}$) | (6.4 ± 0.4) × 10$^5$ | (2.13 ± 0.1) × 10$^5$ | (1.19 ± 0.07) × 10$^6$ |
| $k_{diss\#1}$ (s$^{-1}$) | (2.1 ± 0.4) × 10$^{-4}$ | (7.1 ± 0.1) × 10$^{-2}$ | (1.10 ± 0.07) × 10$^{-1}$ |
| $k_{ass\#2}$ (s$^{-1}$) | n/a | (1.8 ± 0.2) × 10$^3$ * | (2.70 ± 0.09) × 10$^{-2}$ |
| $k_{diss\#2}$ (s$^{-1}$) | n/a | (6.6 ± 0.4) × 10$^{-4}$ | (4.5 ± 0.1) × 10$^{-4}$ |
| $K_{d\,1}$ (M) | (3.3 ± 0.8) × 10$^{-10}$ | (3.3 ± 0.8) × 10$^{-7}$ | (9.2 ± 0.6) × 10$^{-8}$ |
| $K_{d\,2}$ (no unit) | n/a | (3.7 ± 0.6) × 10$^{-7}$ ** | (1.66 ± 0.09) × 10$^{-2}$ |
| $K_{dapp}$ (M) | (3.3 ± 0.8) × 10$^{-10}$ | n/a | (1.5 ± 0.2) × 10$^{-9}$ |
| S. D. of residuals (RU) | 6.177 | 1.080 | 0.922 |
| Z1 statistic | 45.0 | 35.4 | 30.4 |
| Z2 statistic | 4.252 | 2.562 | 2.223 |

* in M$^{-1}$s$^{-1}$
** in M

The interaction of the coiled-coil induced TβRIIED-K5/TβRIIED-E5 dimer with TGF-β1 was best described by a one-to-one stoichiometry model including a rearrangement step (FIG. 5E, Table 2), suggesting that a preformed dimeric TβRIIED binds to TGF-β1 and undergoes a rearrangement. To confirm this, the apparent $K_d$ for the interaction of TβRI-IED-E5 with synthetic K5 coil (reported as 0.5 nM by De Crescenzo, G. et al., *J. Mol. Biol.*, 328(5):1173-83 (2003)) was used to calculate the percent of total TβRIIED that is dimerized when equimolar amounts of TβRIIED-E5 and TβRIIED-K5 are preincubated. This calculation assumes that the coiled-coil interaction, when occurring between TβRI-IED-K5 and TβRIIED-E5, has the same affinity ($K_d$) as the interaction of TβRIIED-E5 with synthetic K5 coil. Based on this calculation, the percent of dimer varied from 80 to 91% for the range of concentrations used in FIG. 5D, suggesting that TβRIIED is binding as a dimer to TGF-β1, i.e., one TβRIIED domain, within the coiled-coil induced dimer, binds to one monomer of TGF-β1 followed by the binding of the other TβRIIED domain to the other monomer of the same TGF-β1 dimer.

Additionally, since the same TGF-β1 surface was used for both monomeric TβRIIED-K5 and coiled-coil induced TβRI-IED-K5-TβRIIED-E5 dimer injections, if both kinetic models depicting the interactions between TGF-β1 and the binding proteins are adequate, the calculated amount of active TGF-β1 on the surface (which is a global parameter determined during data fitting) should be the same. The amount of active TGF-β1 was determined to be 62.5+/−2 RUs when fitting the monomeric TβRIIED-K5 interaction with a two-to-one stoichiometry model. In the case of TβRIIED-K5/TβRIIED-E5 data, the amount of TGF-β1 was 61.7+/−1 RUs with the rearrangement model, 40+/−3 RUs with the simple model, and 145+/−4 RUs with the avidity model. This observation further supports the validity of the two-to-one stoichiometry model for the interaction of TGF-β1 with monomeric TβRIIED-K5 and the rearrangement model for the interaction of TGF-β1 with the coiled-coil induced TβRIIED-K5/TβRIIED-E5 dimer.

3. Binding of MP-TβRIIIED Fusion Protein and MP-TβRIIIED-K5/TβRIIED-E5 Coiled-Coil Induced Dimer to TGF-β1

The kinetics of binding of TGF-β1 to MP-TβRIIIED-K5 fusion protein (SEQ ID NO:9) was evaluated as described in Example 3. Also, the effect of dimerizing MP-TβRIIIED-K5 with TβRIIED-E5 on the binding interaction with TGF-β1 was studied. TGF-β1 was coupled to the biosensor surface (less than 75 RUs) and either monomeric MP-TβRIIIED-K5 or MP-TβRIIIED-K5 dimerized with TβRIIED-E5 through the coiled-coil interaction was injected over the biosensor surface.

Figure 6A:
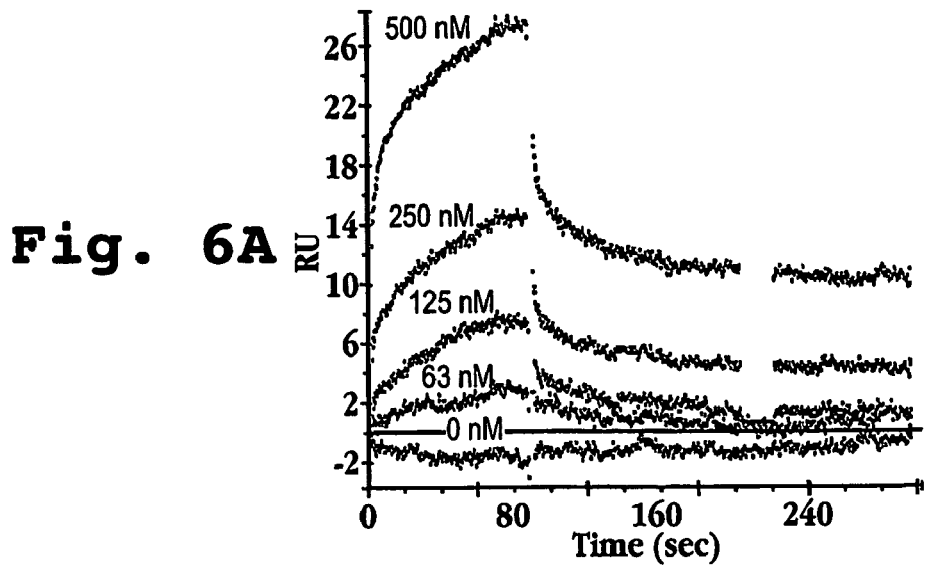
FIGS. 6A-6D are biosensor sensorgrams showing binding interactions between TGF-β1 and MP-TβRIIIED-K5 or MP-TβRIIIED-K5 preincubated with equimolar concentration of TβRIIED-E5.
Figure 6B:
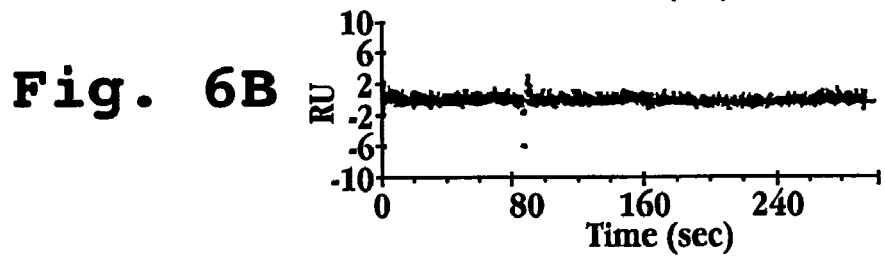
Figure 6C:
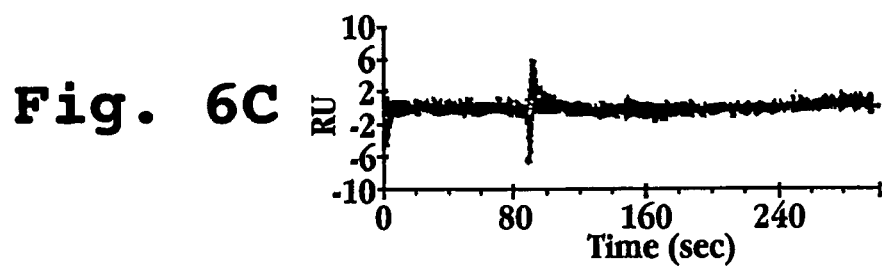

FIGS. 6A-6D show the results of these studies. Global fitting of both sets of sensorgrams indicated that the interactions of TGF-β1 with monomeric MP-TβRIIIED-K5 and with MP-TβRIIIED-K5/TβRIIED-E5 dimer deviated from a simple binding mechanism. In FIG. 6A, different concentrations of MP-TβRIIIED-K5 monomeric fusion protein ranging from 62.5 nM to 500 nM were injected over 75 RUs of coupled TGF-β1 and over a control surface. The points are the resonance units obtained after data preparation as described in Example 2, and the solid lines represent the fit when integrating all the curves simultaneously using a rearrangement model. FIGS. 6B-6C show residuals from the fit of the interaction data using a rearrangement model (FIG. 6B) and a simple one-to-one model (FIG. 6C). Global analysis of the TGF-β1/MP-TβRIIIED-K5 interaction using a simple model gave the following kinetic constants: the apparent on-rate was estimated to be $(5.0\pm0.2)\times10^4$ $M^{-1}s^{-1}$ and the apparent off-rate to be $(2.5\pm0.1)\times10^{-3}$ $s^{-1}$, resulting in an apparent $K_d$ of 49 nM (the standard deviation of the residuals being 0.527). The apparent $K_d$ determined using the rearrangement model was estimated to be 86 nM (the standard deviation of the residuals being 0.359).

Figure 6D:
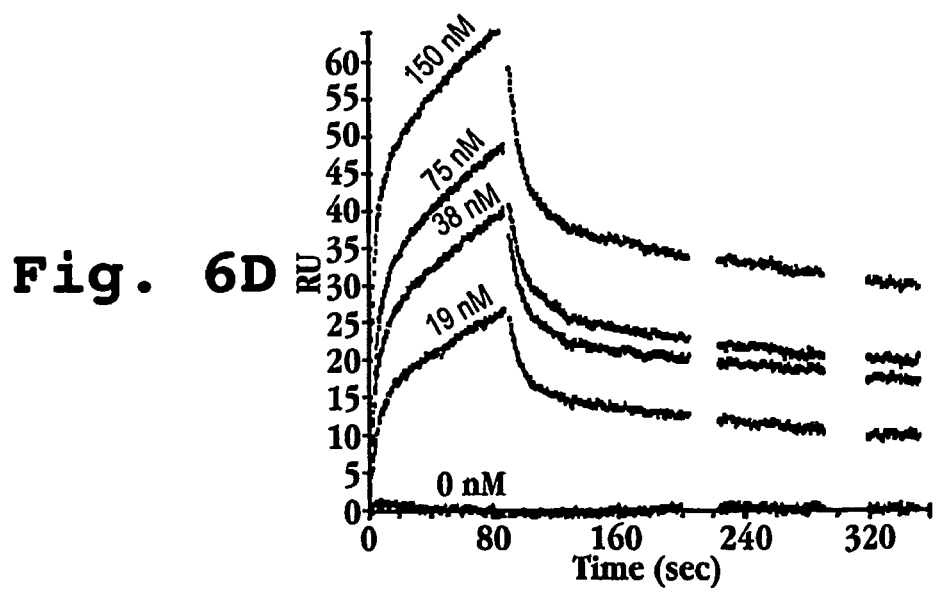

FIG. 6D shows the interaction sensorgram for different concentrations of MP-TβRIIIED-K5/TβRIIED-E5 coiled-coil dimer ranging from 18.8 nM to 50 nM injected over the same TGF-β1 surface as used with MP-TβRIIIED-K5 alone. The points are the resonance units obtained after data preparation.

A comparison of non-dimerized MP-TβRIIIED-K5 (FIG. 6A) and the MP-TβRIIIED-K5/TβRIIED-E5 dimer (FIG. 6D) binding to TGF-β1 indicated that coiled-coil induced dimerization resulted in an increase in the apparent affinity, as evidenced by 6 RUs versus 60 RUs being reached at the end of the injection of 125 nM MP-TβRIIIED-K5 (FIG. 5A) versus 150 nM MP-TβRIIIED-K5/TβRIIED-E5 (FIG. 6D), respectively. This marked RU difference is not likely a result solely from the increase in the molecular weight of the dimer versus the monomer, but more probably a result from a multiple contact mode of binding for the heterodimer. Therefore, the coiled-coil induced heterodimer is likely binding to both TβRII and TβRIII sites within one TGF-β1 dimer, thereby affecting the affinity by a mechanism similar to that observed for coiled-coil dimerized TβRIIED.

TABLE 3

Kinetic and thermodynamic constants for TGF-β1 (coupled) Interacting with K5 tagged TβRIIED or with untagged CtermTβRIIED. (Done in triplicate).

| Kinetic and thermodynamic Parameters | Model: rearrangment Cterm-TβRIIED-K5coil | Model: Simple Cterm-TβRIIED-K5coil | Model rearrangement CtermTβRIIED |
|---|---|---|---|
| $k_{ass\#1}$ ($M^{-1}s^{-1}$) | $(6.4 \pm 0.3) \times 10^4$ | $(5.0 \pm 0.2) \times 10^4$ | $(7.5 \pm 0.1)10^4$ |
| $K_{diss\#1}$ ($s^{-1}$) | $(4.4 \pm 0.3) \times 10^{-2}$ | $(2.5 \pm 0.1) \times 10^{-3}$ | $(5.35 \pm 0.09)10^{-2}$ |
| $k_{ass\#2}$ ($s^{-1}$) | $(1.10 \pm 0.04)10^{-2}$ | n/a | $(2.9 \pm 0.4)10^{-3}$ |
| $k_{diss\#2}$ ($s^{-1}$) | $(1.6 \pm 0.1)10^{-3}$ | n/a | $(2.17 \pm 0.05)10^{-3}$ |
| $K_{d\,1}$ (M) | $(6.7 \pm 0.8) \times 10^{-7}$ | $(4.9 \pm 0.5) \times 10^{-5}$ | $(7.13 \pm 0.3) \times 10^{-7}$ |
| $k_{d\,2}$ (no unit) | $(1.5 \pm 0.2) \times 10^{-1}$ | n/a | $(7.3 \pm 0.3) \times 10^{-1}$ |
| $K_{dapp}$ (M) | $(8.6 \pm 2.1) \times 10^{-8}$ | $(4.8 \pm 0.5) \times 10^{-8}$ | $(30.2 \pm 2.5) \times 10^{-8}$ |
| Standard deviation of residuals (RU) | 0.359 | 0.527 | n/a |
| Z1 statistic | 26.9 | 34.2 | n/a |
| Z2 statistic | 4.88 | 5.28 | n/a |

In another embodiment of the invention, an alternative approach to achieving coiled-coil induced dimerization of TβRIIED is provided. In this embodiment, a dimeric coil is used to act as an adaptor to bridge two proteins. For example, in studies herein, a dimer coil referred to as K5ox, was obtained by oxidizing a K5 subunit that has Cys at the N-terminus (SEQ ID NO:20) in order to form a K5 covalent dimer capable of bridging two TβRIIED-E5 proteins. In a study done in support of this embodiment, described in Example 3, the TβRIIED-E5 fusion protein (SEQ ID NO: 1) was preincubated with various concentrations of K5ox (SEQ ID NO:20) and the solutions were injected over immobilized TGF-β1 and control biosensor surfaces. The results are shown in FIG. 7 and indicate that when TβRIIED-E5 (300 nM) was incubated with 50 (sensorgram 2) and 150 nM (sensorgram 3) of K5ox (6:1 and 2:1 TβRIIED-E5:K5ox molar ratio, respectively), the sensorgram differed greatly from that corresponding to the injection of TβRIIED-E5 alone (sensorgram 1). The shape of sensorgrams 2 and 3 were similar to that obtained for the TβRIIED-E5/TβRIIED-K5 dimer that resulted from the E5/K5 interaction (compare FIG. 5D and FIG. 7 (sensorgram 2 and 3)). In contrast, when an excess of K5ox (900 nM) was added to TβRIIED-E5 (3:1 ratio), the binding was similar to that of TβRIIED-E5 alone (compare sensorgrams (1) and (4) in FIG. 7). These results suggest that, when at a concentration below that of TβRIIED-E5, K5ox bound to TβRIIED-E5 with a one-to-two stoichiometry, resulting in a dimer with TGF-β1 binding properties similar to those of the TβRIIED-E5/TβRIIED-K5 dimer (slow apparent off-rates). When an excess of K5ox was used, the stoichiometry of binding shifted to one K5ox to one TβRIIED-E5, resulting in a complex that has the same TGF-β1 binding characteristics as monomeric TβRIIED-E5 (fast apparent off-rates).

D. Antagonistic Potency

In other studies performed, the ability of the fusion proteins and of the coiled-coil induced dimers to antagonize TGF-β1 signaling was tested. In these studies, described in Example 4, luciferase-transfected mink lung epithelial cells (MLECs) were attached to 96-well plates. TGF-β1 in the presence of a fusion protein or of a coiled-coil induced dimer (heterodimer or homodimer) was added to the cells and incubated overnight. The cells were then lysed and assayed for luciferase activity by measuring luminescence. The activity was expressed as the percent of the activity of TGF-β1 in the absence of the antagonizing fusion protein, homodimer, or heterodimer. The results are shown in FIGS. 8A-8E.

FIG. 8A shows the percent relative luciferase activity as a function of antagonist concentration (nM) for the fusion protein antagonists TβRIIED-K5 (open diamonds) and TβRIIED-E5 (open triangles), and for the antagonist coiled-coil induced dimer TβRIIED-K5/TβRIIED-E5 (equimolar mixture, filled squares). As seen in FIG. 8A, TβRIIED-K5 (open diamonds) and TβRIIED-E5 (open triangles) failed to inhibit TGF-β1-induced receptor signaling, over the concentration range tested (0.1 to 30 nM). The coiled-coil induced dimeric form of TβRIIED, formed by preincubating equimolar concentrations of E5 coiled-tagged TβRIIED and K5 coiled-tagged TβRIIED, was able to block signaling by 50% at a concentration of 7.5 nM.

In order to evaluate if the K5ox-induced dimerization of TβRIIED would have the same effect, 150 nM of TβRIIED-E5 was preincubated with increasing amounts of K5ox. TβRIIED-E5 alone at a concentration of 150 nM (data not shown) and K5ox alone up to a concentration of 100 nM (open squares in FIG. 8B) were unable to antagonize TGF-β1 signaling. However, 150 nM TβRIIED-E5 (filled squares in FIG. 8B), blocked 50% of signaling in the presence of 34 nM K5ox. The reverse experiment (i.e, 150 nM of K5ox preincubated with increasing concentrations of TβRIIED-E5) gave similar results, as shown in FIG. 8C, with an $IC_{50}$ of 53 nM of TβRIIED-E5 in the presence of 150 nM K5ox being observed.

The non-dimerized MP-TβRIIIED-K5 and the coiled-coil induced TβRIIED-E5/MP-TβRIIIED-K5 dimer were also tested for antagonistic potency. FIG. 8D shows the percentage of relative luciferase activity as a function of antagonistic concentration for MP-TβRIIIED-K5 (open squares) and for MP-TβRIIIED-K5/TβRIIED-E5 equimolar mixtures (filled squares). MP-TβRIIIED-K5 alone enhanced TGF-β1 signaling. This enhancement effect was also present when MP-TβRIIIED-K5 was preincubated with equimolar amounts of E5 coil to mask the K5 hydrophobic residues, suggesting that the effect was not coil mediated (data not shown). In contrast, when MP-TβRIIIED-K5 was preincubated with equimolar amounts of TβRIIED-E5 (FIG. 8D, filled squares), the resulting coiled-coil induced dimer was able to block signaling by 50% at a concentration of 40 nM of each ectodomain.

An additional study was conducted in which increasing concentrations of TβRIIED-E5 were preincubated with 150 nM of MP-TβRIIIED-K5. The results are shown in FIG. 8E and indicate that the dimer blocked TGF-β1 signaling by 50% when 7 nM of TβRIIED-E5 was preincubated with 150 nM of MP-TβRIIIED-K5.

In summary, the antagonistic potency of the ectodomains was enhanced by coiled-coil induced dimerization. TβRIIED that was dimerized through coiled-coil interactions, by preincubation of TβRIIED-E5 either with TβRIIED-K5 or with K5ox, was able to block TGF-β1 signaling. The $IC_{50}$s for inhibition of signaling were approximately 7.5 nM and 30 nM for the coiled-coil dimer and for the K5ox dimer, respectively. The higher $IC_{50}$ for the K5ox-induced dimerization is likely due to the fact that K5ox less effectively induces dimerization as compared to simple mixing of the E5- and K5-coil-tagged TβRIIEDs.

Non-dimerized MP-TβRIIIED-K5, at concentrations higher than 150 nM, strikingly enhanced TGF-β1 signaling (FIG. 8D). This enhancement of activity was not due to the presence of the unpaired coil tag since incubation of MP-TβRIIIED-K5 with synthetic E5 coil gave the same results (data not shown).

With respect to the MP-TβRIIIED-K5/TβRIIED-E5 heterodimer, an antagonistic effect was observed (FIG. 8D). As with the TβRIIED coiled-coil induced homodimers, the antagonistic potency of the MP-TβRIIIED-K5/TβRIIED-E5 mixture appeared to be limited by the affinity of the coiled-coil interaction. Indeed, when preincubating equimolar concentrations of both coil tagged ectodomains, TGF-β1 signaling was blocked by 50% when the MP-TβRIIIED-K5 concentration was 40 nM (FIG. 8D). However, when MP-TβRIIIED-K5 was preincubated with a higher concentration of TβRIIED-E5 (150 nM), 50% inhibition of signaling was observed at 7 nM MP-TβRIIIED-K5 (FIG. 8E). This likely results from an increase in the heterodimer population at the same MP-TβRIIIED-K5 concentration.

Thus, coiled-coil induced dimerization can be used as a strategy to enhance the potency of TGF-β1 receptor ectodomains to inhibit cell surface receptor signaling. The coiled-coil induced dimerization strategy provides for monomeric, homodimeric, and heterodimeric forms of the receptor ectodomains that can be rapidly produced and evaluated.

From the foregoing, it can be seen how various objects and features of this aspect of invention are met. Fusion proteins containing the E5 and K5 coils, i.e, TβRIIED-K5, TβRIIED- E5, and MP-TβRIIIED-K5 were prepared and characterized in monomeric form and in dimeric form. Homodimers and heterodimers of the fusion proteins readily form due to interaction of the coil tags. The homodimers and heterodimers are able to bind TGF-β1 and to block TGF-β1 signaling in vitro. The inhibition of TGF-β1 by the homodimers and heterodimers allows their use as biopharmaceutical agents and in screening assays for compounds capable of inhibiting TGF-β1 binding.

The studies described above were completed using the ectodomains of human TGF-β type II and rat TGF-β type III cell surface receptors. It will be appreciated that TGF-β receptor ectodomains from other species are also contemplated and suitable for use. TGF-β ectodomain sequences of mouse, rat, pig, chicken are reported in the literature (Guimond, A. et al., FEBS, 515:13-19 (2002)). These sequences are incorporated by reference herein. It will also be appreciated that the fusion proteins can be constructed using all or selected portions of the receptor ectodomains. For example, portions of the receptor having biological activity can be selected for use in the fusion protein. More generally, receptor ectodomains having at least about 80% sequence identity, more preferably 85%, still more preferably 90%, and most preferably 95%, to the ectodomain sequences described herein are contemplated for use.

E. Methods of Use

In another aspect the invention provides for a screening assay for selection of a compound capable of inhibiting the binding activity of TGF-β1 to one or more of its receptors. To conduct the assay, a coiled-coil homodimer or heterodimer protein is prepared, as described above. The protein is comprised of (i) an extracellular domain of a first transmembrane receptor and a first peptide subunit of an α-helical coiled-coil; and (ii) an extracellular domain of (a) the first transmembrane receptor or (b) a second transmembrane receptor, and a second peptide subunit of the α-helical coiled-coil. With specific reference to TGF-β receptors, the coiled-coil dimer is comprised of first and second fusion proteins. The first fusion protein is comprised of an ectodomain or portion of an ectodomain from TβRII or TβRIII receptors tagged with either a K5 or E5 coiled-coil subunit peptide. The second fusion protein is comprised of either the same receptor ectodomain present in the first fusion protein (to achieve a receptor homodimer) or a different ectodomain or portion of an ectodomain from TβRII or TβRIII receptors than that used in the first fusion protein (to achieve a receptor heterodimer). The ectodomain in the second fusion protein is tagged with the opposing coiled-coil subunit peptide from that used in the first fusion protein.

The coiled-coil homodimer or heterodimer is incubated with a test compound in the presence of a ligand for the receptor ectodomains within the coiled-coil dimer. For example, for dimers prepared with ectodomains from a TGF-β receptor, a suitable ligand is an isoform of TGF-β having binding affinity to the ectodomain(s) within the coiled-coil dimer. The ability of the test compound to inhibit interaction between the receptor ligand and the coiled-coil dimer is measured by a suitable method known to those of skill in the art such as a competitive binding assay, SPR using a biosensor, or the like. For example, in a competitive binding assay, the coiled-coil dimer can be attached to a 96 well plate and then incubated with the test compound. Radiolabelled TGF-β ligand is then added to the plate and allowed to incubate. After washing to remove unbound ligand, the amount of bound TGF-β is assayed. Comparison of the amount of bound TGF-β in the presence and absence of the test compound permits determination of the ability of the test compound to inhibit TGF-β binding to the receptor, where a decrease in the amount of TGF-β is indicative of a test compound having inhibition activity.

A test compound's ability to inhibit TGF-β binding can also be measured using a biosensor, where the TGF-β ligand is attached to the biosensor surface. The ability of the test compound to block the interaction between the coiled-coil induced receptor dimer and the immobilized ligand is assayed.

In yet another aspect of the invention, methods of treating conditions characterized by an overexpression of TGF-β are contemplated. Overexpression of TGF-β is a characteristic of, for example, tissue fibroproliferative disorders. Tissue fibrosis is a pathological state characterized by a deleterious accumulation of extracellular matrix. For example, in progressive glomerular disease of the kidney, extracellular matrix accumulates in the mesangium or along the glomerular basement membrane, eventually causing end-stage disease and uremia. Similarly, adult or acute respiratory distress syndrome involves a deleterious accumulation of matrix materials in the lung, while cirrhosis of the liver is characterized by a deleterious matrix accumulation evidenced by scarring of the liver. Another condition characterized overexpression of TGF-β, and thus by the deleterious accumulation of extracellular matrix, is diabetic nephropathy, which is now the most common cause of progressive kidney failure. Similarly, human mesangial proliferative glomerulonephritis and postradiation fibrosis are characterized by excess TGF-β and overproduction of connective tissue. Tumor metastasis are also characterized by excess TGF-β expression.

Thus, uncontrolled synthesis of TGF-β is one factor which caused the deleterious accumulation of extracellular matrix that underlies the development of issue fibrosis. Progressive fibrosis of the kidney, liver, lung, heart, bone marrow, and skin is both a major cause of suffering and death and an important contributor to the cost of health care. TGF-β also stimulates cells to produce more proteins, including collagen, biglycan, decorin, and fibronectin, and to inhibit enzymes which degrade these proteins.

Accordingly, the invention contemplates a method of treating these and other conditions characterized by production and/or overexpression of TGF-β by administering a coiled-coil induced receptor dimer, homodimer or heterodimer, comprised of two ectodomains, or portions of ectodomains, which can be the same (for a homodimer) or different (for a heterodimer), each ectodomain tagged with a subunit of an α-helical coiled-coil. The coiled-coil homodimer or heterodimer is effective to inhibit TGF-β binding to the cell-surface receptor, thereby preventing the downstream cascade of events initiated by TGF-β receptor binding.

Determination of the appropriate dose regimen of a coiled-coil homodimer or heterodimer for a given patient is well within the skill of the attending physician. Since the proper dose varies from person to person based on the age and general state of health, it is a common practice of physicians to "dose-titrate" the patient; that is, to start the patient on a dosing regimen which is at a level below that required to produce the desired response, and gradually increase the dose until the desired effect is achieved.

The invention also contemplates a kit comprising a coiled-coil dimer based on a TGF-β ectodomain for use in identifying compounds capable of inhibiting and/or competing with TGF-β receptor binding. The kit is comprised of a first container holding a coiled-coil dimerized receptor ectodomain homodimer or heterodimer, comprised of two ectodomains, or portions of ectodomains, which can be the same (for a homodimer) or different (for a heterodimer), each ectodomain tagged with a subunit of an α-helical coiled-coil. It will be appreciated that rather than supplying the coiled-coil dimerized receptor ectodomain, the kit can provide a container with a first fusion protein, a container with a second fusion protein; the two fusion proteins combined by the user prior to use to form the coiled-coil dimerized receptor ectodomain. The kit also includes a container holding a ligand (the term ligand generally referring to a binding partner) for the coiled-coil dimerized receptor, for example, the ligand can be a protein or a peptide. A specific example of a ligand for a coiled-coil dimer formed using a TGF-β ectodomain is TGF-β. The ligand is labeled for detection by a conventional technique; the label can be a radiolabel, a fluorescent label, a photolabel, etc. The kit also includes written instructions that describe use of the kit components, where the user mixes all or a portion of the coiled-coil dimer with the labeled-ligand in the presence and/or in the absence of one or more test compounds. The ability of the test compound(s) to inhibit binding of the coiled-coiled dimer to the labeled ligand is detected. The instructions can also provide guidance for a washing and/or separation step, if needed.

III. Cytoplasmic Domain Fusion Protein Preparation and Characterization

In another aspect, the invention includes a fusion protein comprised of a cytoplasmic domain of a transmembrane bound receptor and a peptide subunit of a coiled-coil dimer. The fusion protein is preferably constructed using the soluble, intracellular domain of a cell receptor; that is, the transmembrane spanning segment of the receptor is excluded. Fusion proteins comprised of a cytoplasmic domain derived from cell surface receptors for TGF-β and for epidermal growth factor, joined to a peptide subunit of an α-helical coiled-coil, were prepared, as will now be described.

As detailed in Example 5, fusion proteins comprised of a kinase domain from TGF-β type II receptor having a sequence identified herein as SEQ ID NO:21 and a NH$_2$-terminal E-coil (SEQ ID NO:5) of a coiled-coil dimer were prepared. A second fusion protein comprised of a kinase domain from TGF-β type I receptor having a sequence identified herein as SEQ ID NO:22 and a NH$_2$-terminal K-coil (SEQ ID NO:8) of a coiled-coil dimer was prepared as described in Example 5. In brief, the coding sequences for the receptor domains were PCR amplified to introduce the coiled-coil tail. The amplified sequences were ligated to a pBlueBac vector and used to express the proteins in insect cells. The recombinant fusion proteins were purified by affinity chromatography and characterized by electrophoresis.

Figure 9:
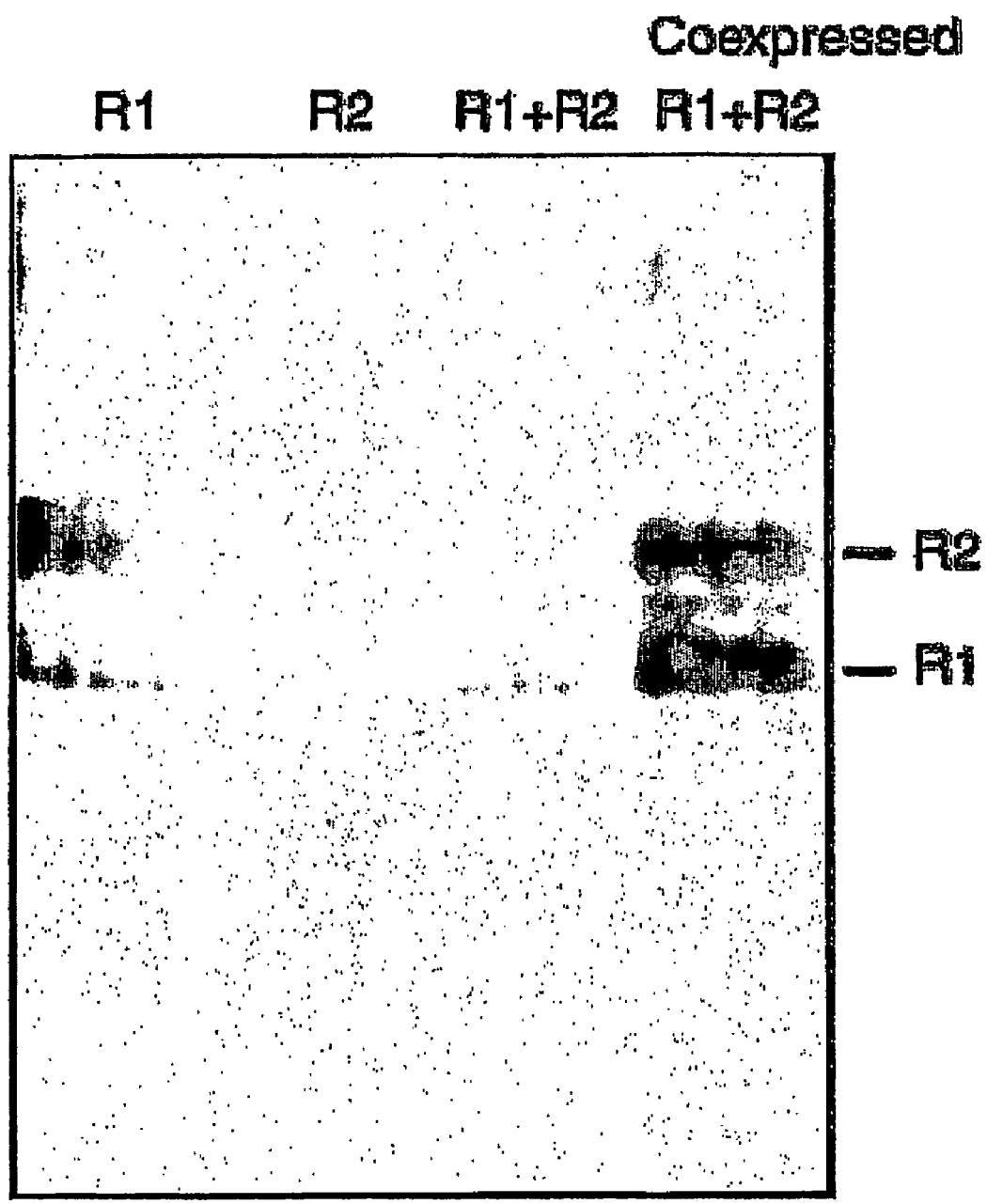
FIG. 9 is an SDS-PAGE gel electrophoresis of the kinase domains of TGF-β receptor I or receptor II tagged with a peptide subunit (K5 or E5) of a coiled-coil polypeptide, where Lane 1 is TGF-β receptor I joined with K5 peptide subunit; Lane 2 is TGF-β receptor II tagged with the E5 peptide subunit; Lane 3 is a mixture of TGF-β receptor I-K5 and TGF-β receptor II-E5; and Lane 4 is a sample of co-expressed TGF-β receptor I-K5 and TGF-β receptor II-E5.

FIG. 9 is an SDS-PAGE gel electrophoresis showing autophosphorylation of the fusion proteins comprised of the kinase domains of TGF-β receptor I or receptor II tagged with a peptide subunit (K5 or E5) of a coiled-coil polypeptide, and of a heterodimer of the two fusion proteins. Each fusion protein or the dimer were incubated with P$^{33}$-gamma ATP and then electrophoresed. Lane 1 in the figure corresponds to TGF-β receptor I cytoplasmic domain joined with a K5 peptide subunit; Lane 2 corresponds to TGF-β receptor II cytoplasmic domain tagged with the E5 peptide subunit; Lane 3 is a mixture of TGF-β receptor I-K5 and TGF-β receptor II-E5; and Lane 4 is a sample of co-expressed TGF-β receptor I-K5 and TGF-β receptor II-E5. As seen, Lane 4 corresponding to the heterodimer shows the most autophosphorylation, indicating that the kinase domains when presented as a coiled-coil heterodimer are biologically active, i.e., are in an orientation that promotes cross-phosphorylation, the event that initiates signaling.

Fusion proteins comprised of epidermal growth factor receptor (EGFR) erbB1 cytoplasmic domain (CD) were prepared, as described in Example 6. DNA constructs encoding for erbB1 were ligated to DNA constructs for E5 or K5 and subcloned into a expression vector to generate an EGFR erbB1-K5 (SEQ ID NO:31) protein and an EGFR erbB1-E5 (SEQ ID NO:34) fusion protein. The amino acid sequence of the erbB1-K5 cytoplasmic domain fusion protein is shown in FIG. 10A (erbB1CD-K5) and the amino acid sequence of the erbB1-E5 cytoplasmic domain (erbB1CD-E5) fusion protein is shown in FIG. 10B. FIG. 10A shows the amino acid sequence of the erbB1CD-K5 fusion protein (SEQ ID NO:31). erbB1CD-K5 residues 1 to 6 (underlined) correspond to a 6 amino-acid linker (SEQ ID NO:32); erbB1CD-K5 residues 7 to 41 correspond to the K5 coil (SEQ ID NO:8); erbB1CD-K5 residues 42 to 48 (underlined) correspond to 7 amino-acid linker (SEQ ID NO: 33); erbB1CD-K5 residues 49 to 590 correspond to residues 669 to 1210 comprising the cytoplasmic domain of the human erbB1 sequence according to the numbering used in the Swiss Protein database (accession number: P00533); erbB1CD-K5 residues 591 to 596 (underlined) correspond to a 6 amino-acid His tag peptide sequence.

FIG. 10B shows the amino acid sequence of the erbB1 cytoplasmic domain—E5 (erbB1CD-E5) fusion protein (SEQ ID NO:34). erbB1CD-E5 residues 1 to 6 (underlined) correspond to a 6 amino-acid linker (SEQ ID NO:32); erbB1CD-E5 residues 7 to 41 correspond to the E5 coil (SEQ ID NO:5); erbB1CD-E5 residues 42 to 48 (underlined) correspond to 7 amino-acid linker (SEQ ID NO:33); erbB1CD-E5 residues 49 to 590 correspond to residues 669 to 1210 comprising the cytoplasmic domain of the human erbB1 sequence according to the numbering used in the Swiss Protein database (accession number: P00533); erbB1CD-E5 residues 591 to 596 (underlined) correspond to a 6 amino-acid His tag peptide sequence.

Figure 10C:
FIGS. 10C-10D are Western blots of SDS-PAGE gels showing the results of AG1478 inhibitor assays on human embryonic kidney 293 cells transfected with different erbB1 (EGFR) constructs: Lanes 1-2: erbB1I kinase domain without (Lane 1, control) and with (Lane 2) inhibitor AG1478; Lanes 3-4: erbB1-K5/erbB1-E5 coiled coil dimer without (Lane 3, control) and with (Lane 4) inhibitor; Lanes 5-6: full-length erbB1 (positive control) without (Lane 5) and with (Lane 6) inhibitor.
Figure 10D:
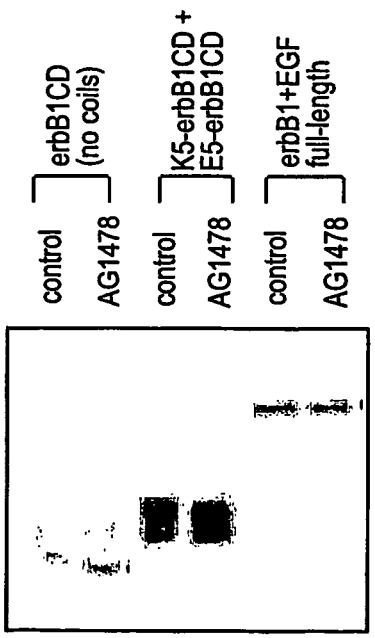

As described in Example 6B, plasmids encoding for the cytoplasmic domain of erbB1, for the fusion proteins (erbB1CD-K5 and erbB1CD-E5), and for the full length erbB1 were transfected into human embryonic kidney 293 cells. After transfection, the erbB1 kinase inhibitor AG1478 was added. Western blot analysis of the cell lysates was done and the results are shown in FIGS. 10C-10D. FIG. 10C is a Western blot for detection of phosphotyrosine, to determine the effect of AG1478 inhibitor on EGFR autophosphorylation. FIG. 10D is an anti-erbB1 Western blot showing the amount of transfected EGFR in each sample. Lanes 1-2 in FIGS. 10C-10D correspond to cell lysates transfected with erbB1 kinase domain without coils, where Lane 1 was a control not treated with the AG1478 inhibitor and Lane 2 was treated with AG1478 inhibitor. The inhibitor had little or no effect on the phosphorylation of the non-coiled coil dimerized erbB1 cytoplasmic domain. Lanes 3 and 4 correspond to cells transfected with erbB1-K5 and with erbB1-E5 and untreated with AG1478 inhibitor (Lane 3) or treated with inhibitor (Lane 4). Lanes 5 and 6 correspond to cells transfected with full length erbB1 and not treated with inhibitor (control, Lane 5) or treated with inhibitor (Lane 6) followed by EGF stimulation. The inhibition of autophosphorylation by the inhibitor was observed with full-length erbB1 (Lane 6) and with the coiled-coil dimerized erbB1 cytoplasmic domain (Lane 4), but not with the erbB1 cytoplasmic domain without coils (Lane 2). This indicates that coiled-coil dimerization of erbB1 renders it more sensitive to erbB kinase inhibitors. That is, the inhibition profile resembles more closely that of the ligand-activated wild type receptor when the kinase domains are dimerized.

A. Methods of Use

Protein-protein interactions are involved in most cellular responses to environmental stimuli. For example, in signal transduction, protein-protein interactions are used to promote or regulate signal transfer from the plasma membrane, through the cytoplasm, to the nucleus. Tools to modulate these interactions and to study biological responses at the molecular level are desirable, as are methods and assays for screening inhibitors of specific steps in signal transduction pathways. Such inhibitors are candidates for therapeutic agents. As noted above, for TGF-β excess receptor signaling is causally related to disease pathogenesis in fibrotic disorders, immunosuppression, and metastasis. In the TGF-β receptor superfamily of serine-threonine kinase receptors, two transmembrane receptors (Type I and Type II) are needed for signal transduction to occur. Specifically, TGF-β binding to the Type II receptor induces recruitment and orientation of the Type I receptor into the complex, allowing the constitutively active Type II receptor kinase to phosphorylate the Type I receptor. In turn, the Type I receptor kinase phosphorylates downstream substrates of the signalling pathway. Thus, methods and agents for selectively inhibiting signaling from TGF-β receptors would be clinically valuable.

Accordingly, the invention in another aspect provides a method for selecting a compound capable of inhibiting kinase activity. In the method, a coiled-coil protein comprised of a first fusion protein comprised of a receptor peptide having a sequence corresponding to a cytoplasmic domain of a cell surface receptor and a first peptide subunit of an α-helical coiled-coil; and a second fusion protein comprised of a receptor peptide having a sequence corresponding to a cytoplasmic domain of a cell surface receptor and a second peptide subunit of an α-helical coiled-coil is prepared. The receptor peptide can be the same or different in the first and second fusion proteins, resulting in a homodimer or a heterodimer, respectively. In a more specific embodiment, the coiled-coil protein is comprised of (i) a cytoplasmic domain of a TGF-β receptor or an EGF receptor and a first peptide subunit of an α-helical coiled-coil; and (ii) a cytoplasmic domain of (a) the same TGF-β receptor or EGF receptor or (b) a different TGF-β receptor or EGF receptor, and a second peptide subunit of the α-helical coiled-coil. The coiled-coil protein is incubated with a test compound. After incubation for a suitable time, the ability of the test compound to inhibit receptor cross-phosphorylation is measured by a suitable technique, such as using $P^{33}$ gamma ATP followed by SDS gel electrophoresis, or using non-radioactive ATP followed by mass spectrometry analysis of phosphorylation.

In the method, the coiled-coil protein can be either a homodimer or a heterodimer. That is, for a homodimer, the coiled-coil protein can be comprised of two fusion proteins, both fusion proteins having the same kinase domain from, for example, TGF-β receptor I, TGF-β receptor II, or from an EGF receptor, one fusion protein having the K coil subunit, the other having the E coil subunit. The fusion proteins thus dimerize into a homodimer. For a heterodimer, the two fusion proteins will have different cytoplasmic domains of TGF-β or of EGF receptors. Exemplary fusion proteins for a heterodimer are one fusion protein having the kinase domain for TGF-β receptor I and the other having the kinase domain for TGF-β receptor II. The two fusion proteins are dimerized to form a heterodimer.

The invention also contemplates a kit for use in identifying compounds capable of inhibiting or reducing receptor kinase activity and in identifying compounds capable of disrupting binding of the coiled-coil dimerized receptor with interacting ligands, including but not limited to peptides or proteins. The kit is comprised of a coiled-coil dimer, formed of a first fusion protein of a receptor cytoplasmic domain and a first subunit of an α-helical coiled-coil and a second fusion protein of a receptor cytoplasmic domain and a second subunit of an α-helical coiled-coil; the two fusion protein forming a coiled-coil dimer. It will be appreciated that the first and second fusion proteins can be provided in separate containers that are combined by the user to form the coiled-coil prior to use. The kinase domains selected for use in the coiled-coil dimer can provide a homodimer or a heterodimer, and the cytoplasmic domains of the fusion proteins can consist of all or a portion of a receptor cytoplasmic domains. The kit also includes written instructions for use of the kit components, where the user mixes all or a portion of the coiled-coil dimer with a kit-supplied or a user-supplied compound to enable kinase reaction, e.g., labeled ATP, in the presence or in the absence of one or more test compounds. The ability of the test compound(s) to inhibit or enhance the kinase reaction, i.e., auto-phosphorylation, is detected using a conventional technique. The kit can also optionally provide another protein or peptide capable of being phosphorylated by, or binding to, the receptor of interest.

IV. Polynucleotides Encoding the Fusion Proteins and Vectors

In another aspect of the invention, polynucleotides encoding for the fusion proteins described above, that is, the fusion proteins comprised of an ectodomain or a cytoplasmic domain of a transmembrane receptor and a coiled-coil dimer subunit, are provided. The amino acid sequence for the fusion protein is used to generate a corresponding nucleic acid sequence, typically a DNA sequence. The codon usage of the generated DNA sequence can be optimized for expression in a particular host system, as is known in the art. Construction of the DNA sequence is done synthetically by techniques well known in the art.

Also included in the invention is an expression vector containing the fusion protein coding sequences. The expression vector will also typically include expression control elements to achieve expression of the coding regions in a suitable host. The control elements generally include a promoter, translation initiation codon, and translation and transcription termination sequences, and an insertion site for introducing the insert into the vector.

The DNA encoding the fusion protein can be cloned into any number of vectors to generate expression of the protein in the appropriate host system. Additional features can be engineered into the expression vectors, such as leader sequences that promote secretion of the expressed sequences into culture medium. Recombinantly produced protein can be isolated from lysed cells or from the culture media. Purification is done by methods known in the art, such as ion exchange chromatography, affinity chromatography, and the like.

V. Examples

The following examples further illustrate the invention described herein and are in no way intended to limit the scope of the invention.

Example 1

Construction of Expression Vectors for Production of TβRIIED-E5, TβRIIED-K5 and MP-TβRIIIED-K5 Fusion Proteins A. Materials The pcDNA3 vectors containing the cDNA encoding the E5 and K5 coils (pcDNA3-K5coil and pcDNA3-E5coil) and the pcDNA3 vector containing the cDNA encoding for the N-terminally myc-tagged TGF-β type II receptor (pcDNA3-

TβRII) were obtained from The Biotechnology Research Institute (Montreal, Canada). The pcDNA3 vector containing the myc tagged membrane-proximal domain of the TGF-β type III receptor extracellular domain (pcDNA3-MP-TβRIIIED) was prepared as previously described (Pepin, M. C., et al., *FEBS Lett.* 377:368-372, (1995)). All the enzymes were from New England Biolabs Inc. and were used according to the manufacturer's recommendations. All the primers were purchased from Hukabel Scientific Ltd. (Montreal, Quebec, Canada). Recombinant human TGF-β1 and the anti hTGF-βRII antibody were purchased from R&D Systems (Minneapolis, Minn.). Recombinant human TβRIIED, expressed in *E. coli*, purified and refolded (Hart, P. J., et al., 2002) was a generous gift from Dr. Hinck (University of Texas Health Sciences Centre at San Antonio). The expression vector pTT2 was prepared as described elsewhere in De Crescenzo, G. et al., *J. Mol. Biol.*, 328(5):1173-83 (2003).

The BIACORE 3000, CM5 sensor chips, N-hydroxysuccinimide (NHS), N-ethyl-N'-(3-diethylaminopropyl)carbodiimide hydrochloride (EDC) and 1M ethanolamine (pH 8.5) were purchased from BIACORE Inc. (Piscataway, N.J., USA).

B. Construction of the TβRIIED-E5, TβRIIED-K5, and MP-TβRIIIED-K5 Expression Vectors Construction of the pTT2 TβRIIED-E5 vector is described in De Crescenzo, G. et al., *J. Mol. Biol.*, 328(5):1173-83 (2003).

For construction of pTT2 K5coil, the cDNA encoding for the K5 coil was PCR amplified using the pcDNA3-K5coil as template and the following primers:

$K_{for}$
5'-TAGAGCGGCCGCGGTGGCAAGGTATCCG-3'

(SEQ ID NO: 23; NotI restriction site underlined), and $K_{rev}$:
5'-TAGGATCCCTAATGGTGATGATGGTGATGACCGCCCTC TTTAAGT G-3'

(SEQ ID NO: 24; BamHI restriction site underlined).

The resulting fragments were digested with NotI/BamHI and ligated to pTT2 digested with the same enzymes.

For construction of pTT2 TβRIIED-K5, the cDNA encoding for the myc tagged TβRIIED was PCR amplified as described elsewhere (De Crescenzo, G. et al., *J. Mol. Biol.*, 328(5):1173-83 (2003)), digested with HindIII/NotI, and ligated to pTT2 K5coil digested with the same enzymes.

For construction of pTT2 MP-TβRIIIED-K5; the cDNA encoding for the myc tagged MP-TβRIIIED was PCR amplified using the pcDNA3-MP-TβRIII as template, and the following primers:

$III_{for}$
5'-ATGCTAGCGTTGGAGAGATGGCAGTGACATCCC-3'

(SEQ ID NO: 25; NheI restriction site underlined) and $III_{rev}$
5'-TAGAGCGGCCGCCATGGAAAATCTGTGGAGG-3'

(SEQ ID NO: 26: NotI restriction site underlined).

The resulting fragment was digested with NheI/NotI and ligated to pTT2 K5coil digested with the same enzymes.

The pTT2 TβRIIED-E5, pTT2 TβRIIED-K5, and pTT2 MP-TβRIIIED-K5 ligations were then transformed into *Escherichia coli* (DH5α) and the plasmids were purified using the MAXI prep columns (QIAgen, Mississauga, Ontario, Canada). Each construct was verified by sequencing. For quantification, plasmids were diluted in 50 mM Tris-HCl pH 7.4 and the absorbances at 260 and 280 nm measured. Only plasmid preparations with $A_{260}/A_{280}$ ratios between 1.8 and 2.0 were used for transient transfection.

C. Transient Transfections

The vectors were transiently transfected into HEK 293SF cells using polyethylenimine (PEI) as a transfection vehicle as described in De Crescenzo, G., et al. (*J. Mol. Biol.*, 328(5): 1173-83 (2003)). The recombinant proteins were expressed by the transiently transfected cells and secreted into the medium. The cultures were harvested five days after transfection and the medium was clarified by centrifugation at 3500×g for 10 min.

D. TβRIIED-E5, TβRIIED-K5 and MP-TβRIIIED-K5 Fusion Protein Purification

TβRIIED-E5 was purified as described in De Crescenzo, G. et al. (*J. Mol. Biol.*, 328(5):1173-83 (2003)) and shown in FIG. 2. The TβRIIED-K5 and MP-TβRIIIED-K5 fusion proteins were purified using a Ni-NTA Agarose affinity column (2 mL bed volume, QIAgen) by loading the culture medium by gravity flow. The column was then washed two times with 25 mL buffer A (50 mM sodium phosphate, 300 mM NaCl, pH 7.4). Elution was achieved with buffer B (buffer A+100 mM imidazole, pH 7.4, 8 mL fraction collected). The flow through fraction was reloaded twice and eluted using the same conditions as above. Elution fractions (8 mL each) were then individually concentrated (for TβRIIED-K5, this step included buffer exchange for PBS) by using a Centriprep 10 device (Amicon), according to the manufacturer's recommendations. The concentration of the purified fusion proteins was determined with the Coomassie Plus Protein Assay Reagent Kit (Pierce), using bovine serum albumin as the standard. The yields of TβRIIED-E5, TβRIIED-K5, and MP-TβRIIIED-K5 from 500 mL of conditioned media were approximately 766 μg, 570 μg and 600 μg, respectively.

E. Electrophoresis, Western Blotting, Silver Staining, Coomassie Blue Staining

The purity of the fusion proteins was estimated by either Silver staining using the Silver Stain Plus Kit (Bio-Rad) or Coomassie Blue staining after resolving the proteins on 11% or 4-12% gradient SDS-polyacrylamide gels under reducing conditions. The purified proteins were also detected by Western blot (anti-myc 9E10, Santa Cruz) following protein separation on SDS-polyacrylamide gels under reducing and non-reducing conditions. The results are shown in FIGS. 2 and 3, where Western blot detection was done using anti-myc as a primary antibody and horseradish peroxidase conjugated goat anti-mouse as a secondary antibody. In the figures, lane FT corresponds to the flow through after passing the sample medium on the affinity column; lanes W1 and W2 correspond to two column washes with buffer A; lanes 1, 2, and 3 in FIG. 2 correspond to three elutions of TβRIIED-E5 with buffer B. FIG. 3 shows the purification of TβRIIED-K5 and MP-TβRIIIED-K5. In the case of TβRIIED-K5 purification, protein eluted from a Ni-NTA affinity chromatography column was run on 11% SDS-PAGE under non-reducing (A) and reducing conditions (B and C) followed by Western blotting (A and B; primary and secondary antibody as in FIG. 2) or Silver staining (C). After separation with a Centriprep 30 device to remove disulphide-bridged aggregates, a 10 μL aliquot of monomeric TβRIIED-K5 was run on 11% SDS-PAGE under non-reducing conditions and Western blotted (D). A 10 µL of a 1/15 dilution of the sample shown in Lane A was also run for comparison (E). In the case of MP-TβRII-IED-K5 purification, protein eluted from a NI-NTA affinity chromatography column was run on 11% SDS-PAGE under non-reducing conditions, followed by Western blotting (primary antibody: anti-myc, F) and by Silver staining (G).

F. Separation of TβRIIED-K5 Monomers from Higher Order Aggregates

As in the case of TβRIIED-E5, higher order aggregates were observed by Western blot under non-reducing condition for TβRIIED-K5. Monomeric TβRIIED-K5 was prepared as follows. TβRIIED-K5 (320 µg) was diluted in PBS to a final volume of 10 mL and spun in a Centiprep 30 (Amicon). The filtrate was then concentrated using a Centriprep 10, leading to a 500 µL fraction with a TβRIIED-K5 concentration of 555 nM. The efficacy of the separation of oligomers from monomer was estimated by Western blotting (non-reducing conditions) and the protein concentration was determined as described above in 5.

Example 2

Dimerization of TβRIIED-E5 with TβRIIED-K5 and with MP-TβRIIIED-K5

Surface plasmon resonance studies were performed using a BIACORE™ biosensor (see for example U.S. Pat. No. 6,165,335 and related patents) using a running buffer composed of HBS; 20 mM Hepes (pH 7.4), 150 mM NaCl, 3.4 mM EDTA, and 0.05% Tween20 for diluting all the test analytes.

Anti hTGF-βRII antibody was coupled to the CM5 biosensor chip surface using the standard amine coupling procedure and a flow rate set at 5 µL/min. Sequential injections consisted of a 0.05 M NHS/0.2 M EDC mixture (25 µL) followed by an anti hTGF-βRII antibody injection (20 µg/mL) in 10 mM acetic acid (pH 4.0) until the desired coupled amount was reached (more than 3500 RUs). A solution of 0.1 M ethanolamine-HCl (pH 8.5, 35 µL) was then used to block the remaining activated carboxyl groups. A control dextran surface was also generated by replacing the anti hTGF-βRII antibody solution with running buffer.

Three studies were then performed at a flow rate of 5 µL/min:

1—MP-TβRIIIED-K5 (200 nM, 25 µL) was injected ("1" in FIG. 4A), followed by a TβRIIED-E5 injection (200 nM, 25 µL; "2" in FIG. 4A) and another MP-TβRIIIED-K5 injection (200 nM, 25 µL; "3" in FIG. 4A) over the anti TGF-βRII antibody and the control surfaces.

2—Untagged hTβRII ED (1 µM, 25 µL) was injected ("1" in FIG. 4B) and followed by a MP-TβRIIIED-K5 injection (200 nM, 25 µL; "2" in FIG. 4B) over the anti TGF-βRII antibody and the control surfaces.

3—Solutions with five different TβRIIED-E5 concentrations (31, 62, 125, 250, 500 nM, 15 µL each; ("1-5" in FIG. 4C) were successively injected and were followed by a TβRIIED-K5 injection (50 nM, 15 µL; ("6" in FIG. 4C) over the anti TGF-βRII antibody and the control surfaces.

Regeneration between the different experiments was performed by two pulses of HCl at 20 mM (25 µL at 100 µL/min), followed by an EXTRACLEAN and a RINSE procedure performed according to the BIACORE manual. The results are shown in FIGS. 4A-4C.

Example 3

Binding Kinetics of TβRIIED-K5 and MP-TβRIIIED-K5 Fusion Proteins

A. Immobilization of TGF-β1 on CM5 Biosensor Chips

TGF-β1 surfaces and control dextran surfaces on CM5 sensor chips were prepared as described elsewhere (De Crescenzo, G. et al., *J. Biol. Chem.* 276, 29632-29643 (2001)) using a standard amine coupling procedure.

B. Kinetic Assays

1. Injections of TβRIIED-K5, or Equimolar Mixtures of TβRIIED-K5 and TβRIIED-E5, over TGF-β1

All the kinetic experiments were carried out at 25° C. with a flow rate of 5 µL/min in the case of TβRIIED-K5 injections, and 50 µL/min in the case of TβRIIED-K5-TβRIIED-E5 mixture injections. Different concentrations of TβRIIED-K5 (9.8, 14, 8, 22.2, 33.3, 50 nM), or TβRIIED-K5 mixed with equimolar concentrations of TβRIIED-E5 (0 to 50 nM), were randomly injected in duplicate over a TGF-β1 surface as well as over a control surface (240 second injections), following which the analyte solution was replaced by buffer for 360 seconds. Regeneration of the sensor chip for subsequent injections was accomplished by two pulses of HCl (20 mM, 120 seconds), followed by an EXTRACLEAN procedure performed according to the BIACORE manual. The results are shown in FIGS. 5A-5F.

2. Injections of MP-TβRIIIED-K5, or Equimolar Mixtures of MP-TβRIIIED-K5 and TβRIIED-E5, over TGF-β1

Kinetic experiments were carried out at 25° C. with a flow rate of 100 µL/min. Different concentrations of MP-TβRII-IED-K5 (0 to 500 nM), or MP-TβRIIIED-mixed with equimolar concentrations of TβRIIED-E5 K5 (0 to 150 nM), were randomly injected in duplicate over a TGF-β1 surface as well as over a control surface (150 µL injections), following which the analyte solution was replaced by buffer for at least 210 seconds. Regeneration of the sensor chip for subsequent injections was accomplished by two pulses of HCl (20 mM, 120 seconds), followed by an EXTRACLEAN procedure performed according to the BIACORE manual. The results are shown in FIGS. 6A-6D.

C. Data Preparation and Analysis

Sensorgrams were prepared and globally fit using non-linear least squares analysis and numerical integration of the differential rate equations using the SPRevolution© software package. The data preparation was done using the "double referencing" method (Khaleghpour, K., et al., *Mol. Cell Biol.* 21:5200-5213, (2001)). Briefly, each sensorgram generated using a control surface was subtracted from the corresponding experimental sensorgram and the resulting curve was transformed to concentration units. Finally, the curve corresponding to buffer injection was subtracted from the control surface-corrected curves. Each data set, which consists of sensorgrams from injections of different analyte concentrations over the same surface, was then analyzed using several kinetic models that are available in the SPRevolution© software.

When necessary, the goodness of the fit obtained from the use of different kinetic models was compared using the three following statistical values described elsewhere (Bradley, J. V., *Distribution-Free Statistical Tests*, New-Jersey, (1968)) and were shown to be relevant for discriminating the quality of the fits when using different kinetic models to fit the same data set (De Crescenzo, G. et al., *J. Biol. Chem.* 276, 29632-29643 (2001)):

1) the Standard Deviation of the residuals: S.D.
2) the "+ or − signs" statistic (Z1).
3) the "Run up and down" statistic (Z2).

D. Injections of TβRIIED-E5 Preincubated with K5ox over TGF-β1

1. Oxidation of CGGK5 coil (SEQ ID NO:20) to give K5ox

K5 coil with a cysteine linker (20 mg, SEQ ID NO:20) was dissolved in 2 mL of 100 mM ammonium bicarbonate pH 8.0 at room temperature. Aliquots of the reaction mixture were applied in regular intervals to an analytical C18 HPLC system to monitor the progress of the oxidation. Peptide oxidation was allowed to proceed until 90% completion or up to 12 hours. Acetic acid was added to the mixture at the end of the oxidation to acidify the solution to pH 6. The peptides were then lyophilized and resuspended in PBS buffer prior to use.

Figure 7:
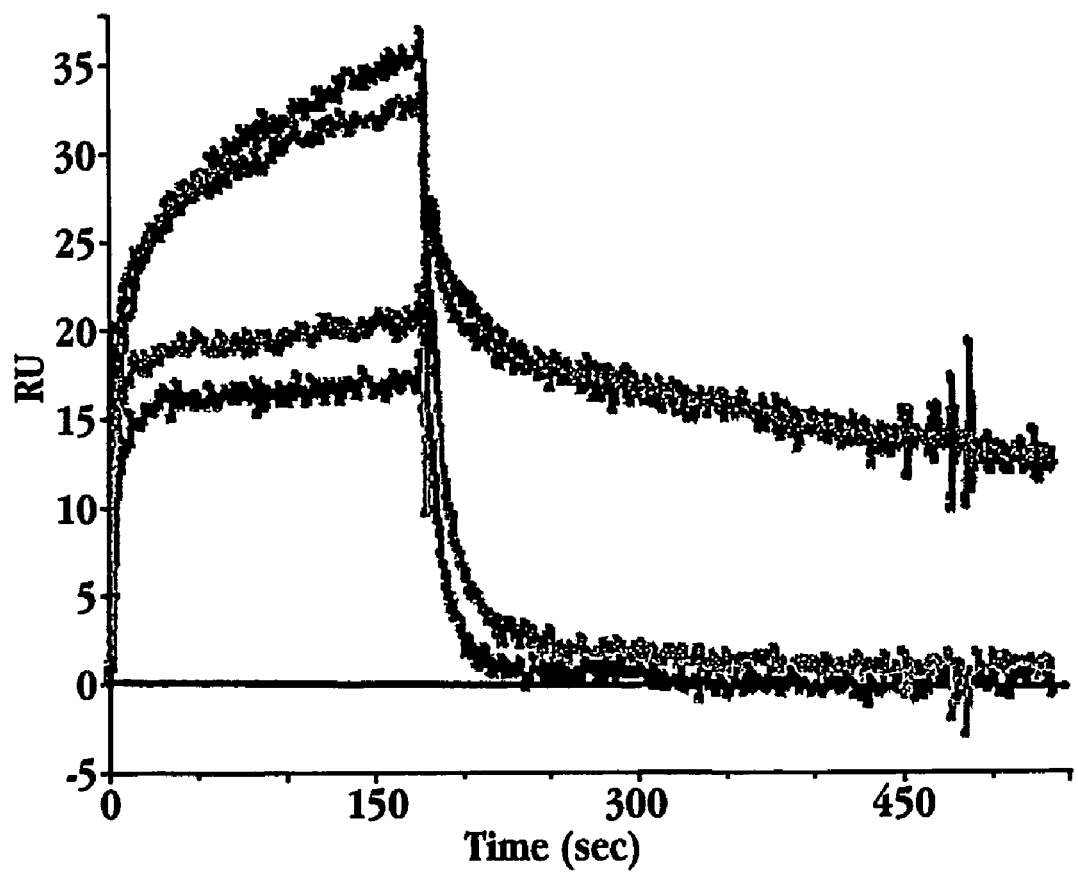
FIG. 7 is a biosensor sensorgram showing binding interactions, in arbitrary resonance units (RUs) as a function of time, of (1) TβRIIED-E5 binding to TGF-β1; and of TβRIIED-E5 binding to TGF-β1 after preincubation of TβRIIED-E5 with (2) 50 nM K5ox; (3) 150 nM K5ox; or (4) 900 nM of K5ox.

2. Binding of TβRIIED-E5 Preincubated with K5ox 300 nM of TβRIIED-E5 was preincubated with various concentrations of K5ox (0, 50, 150, 900 nM) and the resulting solutions were randomly injected in duplicate over a BIAcore biosensor surface with TGF-β1 and over a control surface (15 μL injections), following which the analyte solution was replaced by buffer for 360 seconds. Regeneration of the sensor chip was done as described above. The results are shown in FIG. 7.

Example 4

Antagonistic Potency of Fusion Protein, Homodimers, and Heterodimers

Figure 8A:
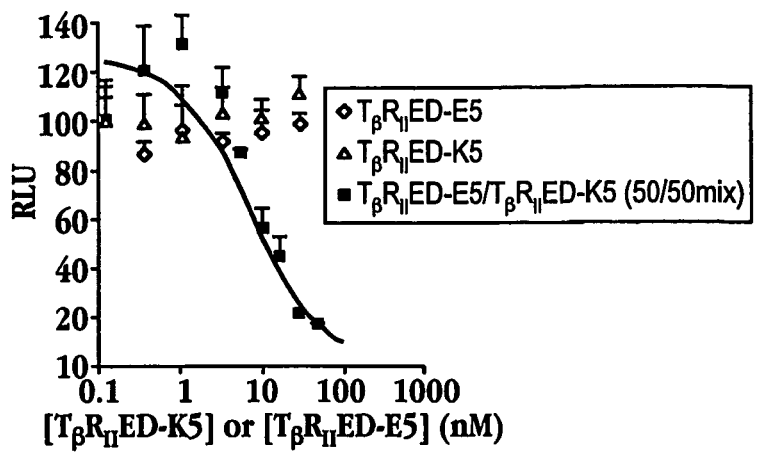
FIG. 8A shows the relative luciferase activity, in percent, as a function of antagonist concentration (nM) for the fusion protein antagonists TβRIIED-K5 (open diamonds) and TβRIIED-E5 (open triangles), and for the antagonist homodimer TβRIIED-K5/TβRIIED-E5 (equimolar mixture, filled squares).
Figure 8B:
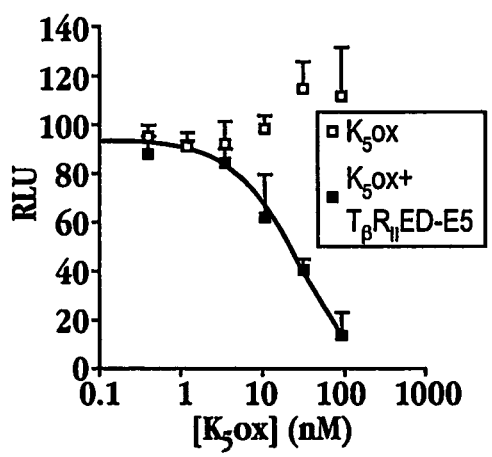
FIG. 8B shows the percent relative luciferase activity as a function of K5ox concentration, in nM, for K5ox alone (open squares) and for TβRIIED-E5 at 150 nM with K5ox (filled squares).
Figure 8C:
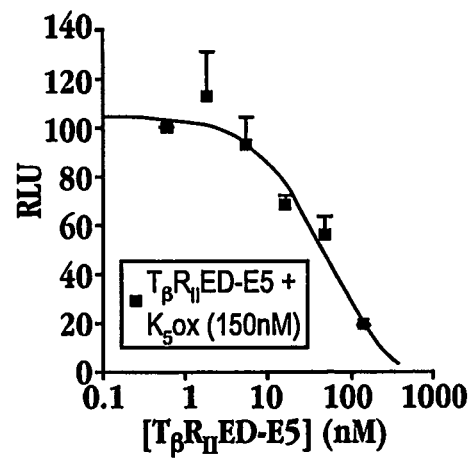
FIG. 8C shows the percent relative luciferase activity for K5ox at 150 nM with various concentrations of TβRIIED-E5.
Figure 8D:
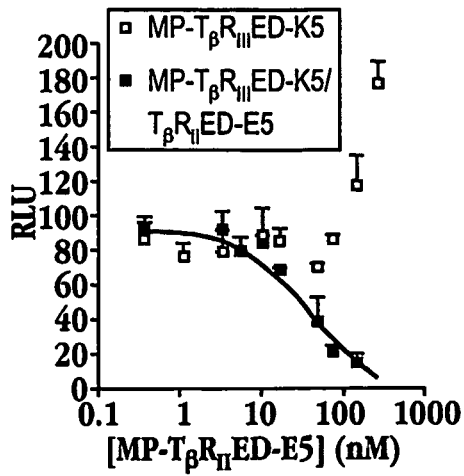
FIG. 8D shows the percent relative luciferase activity for MP-TβRIIIED-K5 (open squares) and for MP-TβRIIIED-K5/TβRIIED-E5 equimolar mixtures (filled squares) at various concentrations.
Figure 8E:
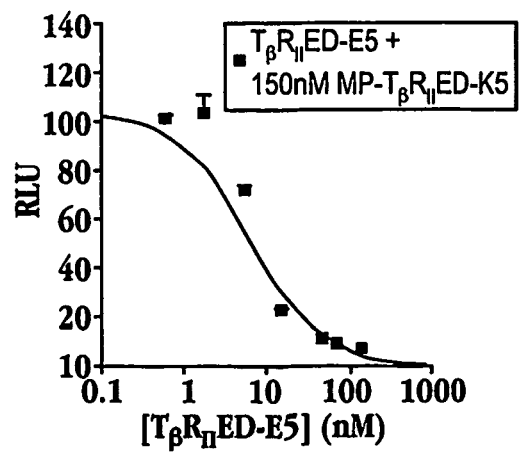
FIG. 8E shows the percent relative luciferase activity for MP-TβRIIIED-K5 at 150 nM with various concentrations of TβRIIED-E5.

Mink lung epithelial cells (MLEC) stably transfected with the PAI-1 promoter fused to the firefly luciferase reporter gene (Abe, M., et al., *Anal. Biochem.* 216:276-284, (1994)) were plated in 96-well tissue culture plates ($2 \times 10^4$ cells/well) in Dulbecco's modified Eagle's medium containing 5% fetal bovine serum (DMEM/5% FBS). The MLECs were allowed to attach for at least 5 hours at 37° C. in a 5% $CO_2$ atmosphere. Cells were then washed with PBS. TGF-β1 (10 pM) in DMEM/1% FBS/0.1% BSA, which was preincubated with the following additions for one hour, was then added to the cells:

A) TβRIIED-K5, TβRIIED-E5, or TβRIIED-K5/TβRI-IED-E5 equimolar mixture at various concentrations (FIG. 8A);
B) TβRIIED-E5 at 150 nM with various concentrations of K5ox, the same series of experiments was also performed in the absence of TβRIIED-E5 (FIG. 8B).
C) K5ox at 150 nM with various concentrations of TβRI-IED-E5 (FIG. 8C).
D) MP-TβRIIED-K5 or MP-TβRIIED-K5/TβRIIED-E5 equimolar mixtures at various concentrations (FIG. 8D).
E) MP-TβRIIED-K5 at 150 nM with various concentrations of TβRIIED-E5 (FIG. 8E).

After an overnight incubation the medium was removed and the cells were washed twice with PBS (200 μL per well). Cells were then lysed and assayed for luciferase activity using the Promega (Madison, Wis., USA) Luciferase Assay Kit according to the manufacturer instructions. Luminescence was measured with a Lumat LB9501 luminometer (Berthold, USA). The activity was expressed as the percent of the activity of TGF-β1 in the absence of antagonist. The results are shown in FIGS. 8A-8E.

When an antagonistic behaviour was observed, the apparent $IC_{50}$ was determined by fitting the experimental data points using the following equation: Response=bottom+(top−bottom)/(1+[Inhibitor]/$IC_{50}$), where Response corresponds to the calculated percent of signaling as defined above and [Inhibitor] being the concentration of antagonist. Top, bottom and $IC_{50}$ were set as parameters and correspond to the maximal and minimal signal values and to the apparent $IC_{50}$ value, respectively. The data were fit by non-linear regression using the Excel™ solver tool by minimizing the sum of (Exp−Response)/Exp where Exp corresponds to the experimental data point value for a given antagonist concentration. The results are in Table 3.

Example 5

Construction of DNA Constructs and Baculovirus Expression Vectors for Production of TGF-β Kinase Domain Fusion Proteins and Dimers Fusion proteins consisting of N-terminal E coil fused to the TGF-β type II receptor kinase domain and N-terminal K coil fused to the TGF-β type I receptor kinase domain were generated by PCR using mammalian expression vectors encoding SEQ ID NO:21 (pAEcoilRII-KD(ΔTM)#5) or SEQ ID NO:22 (pAKcoilRI-KD(ΔTM)#2), respectively, as templates.

The E coil-TGFβ type II receptor kinase domain with a C-terminal His tag was PCR amplified using the following primers. The NheI and HindIII restriction sites are underlined in the primer sequences 5'EIIHis and 3'EIIHis, respectively:

```
5'EIIHis
                                        (SEQ ID NO: 27)
5' ATGCTAGCCACCATGGGAGGTGGTGGTGGCGAGGTA-3'
and 3'EIIHis:
                                        (SEQ ID NO: 28)
5' GAAGCTTTCAGTGATGGTGATGGTGATGTTTGGTAGTGTTTAGGGAG

CC-3'
```

The K coil-TGFβ type I receptor kinase domain with a C-terminal His tag was PCR amplified using the following primers. The NheI and HindIII restriction sites are underlined in the primer sequences 5'KIHis and 3'EIHis, respectively:

```
5'KIHis
                                        (SEQ ID NO: 29)
5'ATGCTAGCCACCATGGGAGGTGGTGGTGGCAAGGTA-3'
and 3'KIHis
                                        (SEQ ID NO: 30)
5'CGAAGCTTTCAGTGATGGTGATGGTGATGCATTTTGATGCCTTCCT

G-3'
```

The resulting fragments were digested with NheI/HindIII and ligated to pBlueBac 4.5 vector (Invitrogen) digested with the same enzymes. Ligations were then transformed into *Escherichia coli* (DH5α) in order to form pBlueBac-TGF-βRIKD-K and pBlueBac-TGFβRIIKD-E. Plasmids were purified using the Maxiprep columns (QIAGEN) and verified by sequencing.

Transfections and Baculovirus expression, using Sf9 insect cells, were done according to MaxBac 2.0 Transfection and Expression manual from Invitrogen. The purification of the recombinant proteins were performed using Ni-NTA agarose affinity column.

Equal amounts of either the TGF-β receptor I-K coil fusion protein, the TGF-β receptor II-E coil fusion protein, a mixture of the two fusion proteins, and or co-expressed TGF-β receptor I-K/TGF-β receptor II-E coil fusion proteins were separately incubated in the presence of P33-gamma ATP for 30 minutes at 30° C. An aliquot of each reaction sample was then electrophoresed under reducing conditions in a 8% acrylamide gel. The gel was dried and the phosphorylated kinases were detected by phosphorimaging. The results are shown in FIG. 9, where the positions of the type I and type II receptors are indicated on the right.

Example 6

Construction of DNA Constructs for Expression of EGFR Cytoplasmic Domain Fusion Proteins and Dimers for Analysis of Inhibitor Sensitivity in Mammalian Cells A. DNA Construct and Fusion Protein Preparation The subcloning strategy used for generating coiled erbB1 cytoplasmic domain expression constructs is indicated below:

STEP 1. erbB1 cytoplasmic domain was PCR amplified with the following XhoI (5') and His tagged NheI (3') primers (restriction sites underlined) from pcDNA3-erbB1 mammalian expression vector encoding the full length cDNA for human EGFR (Genbank accession number: NM 005228).

```
5'XhoIEGFR
                                           (SEQ ID NO: 35)
5' AT CTC GAG CGA AGG CGC CAC ATC GTT CGG AGG 3'

3'NheI EGFR-HIS6C
                                           (SEQ ID NO: 36)
5' GCT AGC TCA GTG ATG GTG ATG GTG ATG TGC TCC AAT

AAA TTC ACT GCT TTC 3'
```

STEP 2. pGemT vector (Promega) containing cDNA encoding K5-TGFβRI (SEQ ID NO:22) or E5-TGFβRII kinase (SEQ ID NO:22) (from pGemT/K5-RIKD and pGemT/E5-RIIKD-E5-TGF, property of Biotechnology Research Institute, National Research Council of Canada) was restricted with XhoI-HindIII (blunt ended) to remove RI or RII kinase domains. XhoI-NheI (blunt ended) restricted erbB1 cytoplasmic domain PCR product (step 1) was inserted at this site.

STEP 3. The Nhe I-Not1 fragment of the resulting pGemt E5- or K5-coiled erbB1CD plasmid was subcloned into the NheI-Not1 site of pTT2 mammalian expression vector (property of Biotechnology Research Institute, National Research Council of Canada) to generate pTT2/K5-erbB1CD construct encoding the erbB1CD-K5 fusion protein (SEQ ID NO:31) and pTT2/E5-erbB1CD construct encoding the E5-erbB1CD fusion protein (SEQ ID NO:34) attached to a carboxy-terminal His tag peptide sequence. After ligation, plasmids were transformed into *E. coli* (DH5α) purified using CONCERT plasmid DNA purification columns (Gibco-BRL) and verified by sequencing.

The subcloning strategy used for generating the native (non-coiled) erbB1 cytoplasmic domain expression construct is indicated below:

STEP 1. erbB1 cytoplasmic domain was PCR amplified with the following XbaI (5') and His tagged NheI (3') primers (restriction sites underlined) from pcDNA3-erbB1 mammalian expression vector encoding the full length cDNA for human EGFR (Genbank accession number: NM 005228).

```
5'XbaIEGFR
                                           (SEQ ID NO: 37)
5' ATT CTA GAC ACC ATG CGA AGG CGC CAC ATC GTT C 3'

3NheI EGFR-HIS6C
                                           (SEQ ID NO: 36)
5' GCT AGC TCA GTG ATG GTG ATG GTG ATG TGC TCC AAT

AAA TTC ACT GCT TTC 3'
```

STEP 2: XbaI and NheI restricted PCR products were subcloned into pTT2 mammalian expression vector (property of Biotechnology Research Institute, National Resource Council of Canada) to generate pTT2/erbB1CD #2 construct encoding the cytoplasmic domain of erbB1 attached to a carboxy-terminal His tag peptide sequence. After ligation, plasmids were transformed into *E. coli* (DH5α) purified using CONCERT plasmid DNA purification columns (Gibco-BRL) and verified by sequencing.

B. Expression and Analysis of EGFR Fusion Proteins and Dimers for Inhibitor Testing Human embryonic kidney 293 cells were plated 5×10 (5) cells/well in a 24-well tissue culture dish the previous day and transfected with 500 ng each of the indicated plasmids: (1) pTT2/erbB1CD #2, (2) pTT2/K5-erbB1CD #2 and pTT2/E5-erbB1CD #3, and (3) pcDNA3-erbB1. In addition to 100 ng CMV-EGFP plasmid, pcDNA3 vector was added as needed for a total of 1.5 ug DNA. Transfection was performed using polyethylenimine as previously described (Durocher, Y. et al., *Nucleic Acids Res.* 30(2):E9 (2002)). After 24 hours of transfection, 500 nM of the erbB1 kinase inhibitor AG1478 (Calbiochem) in DMEM/10% FBS was added and incubated overnight Cells were also incubated with 0.1% DMSO as a vehicle control. Following incubation overnight (~20 hrs), cells were lysed with hot 2% SDS. In the case of transfection with the full length erbB1 cDNA in pcDNA3, cells were treated in the presence of 100 ng/ml EGF (Upstate Biotechnology Inc.) prior to harvesting.

Cell lysates from the various transfections were analyzed by Western blot following protein separation on 8% SDS-polyacrylamide gels under reducing conditions. The results are shown in FIGS. 10C-10D in which phosphotyrosine detection (anti-phosphotyrosine 4G10, Upstate Biotechnology Inc.) was used to measure the effect of inhibitor on EGFR autophosphorylation and EGFR detection by anti-EGF receptor cytoplasmic domain antibody (sc-03, Santa Cruz) was used to measure the level of transfected EGFR in each sample.

Although the invention has been described with respect to particular embodiments, it will be apparent to those skilled in the art that various changes and modifications can be made without departing from the invention.

The invention claimed is:

1. A fusion protein comprising an extracellular domain of a cell surface receptor for transforming growth factor-β and a peptide subunit of an α-helical coiled-coil, the fusion protein having an $IC_{50}$ for inhibition of transforming growth factor-β binding and signalling activity in a nM range.

2. The fusion protein of claim 1, wherein said peptide subunit is a K coil or an E coil having between 3-10 heptad repeat units.

3. The fusion protein of claim 2, wherein said heptad repeat has a sequence selected from the group of sequences identified as SEQ ID NOs:11-17.

4. The fusion protein of claim 1, wherein said peptide subunit has a sequence identified herein as SEQ ID NO:8.

5. The fusion protein of claim 1, wherein said peptide subunit has a sequence identified herein as SEQ ID NO:5.

6. The fusion protein of claim 1, wherein said receptor is selected from the group consisting of transforming growth factor-β type II and transforming growth factor-β type III.

7. The fusion protein of claim 1, associated with a second fusion protein to form a coiled-coil dimer, said second fusion protein comprised of an extracellular domain of a transforming growth factor-β receptor and a second peptide subunit of the α-helical coiled-coil.

8. A polynucleotide comprising a nucleotide sequence encoding the fusion protein of claim 1.

9. A vector comprising the polynucleotide of claim 8.

10. A coiled-coil dimer protein, comprising a first fusion protein comprised of an extracellular domain of a cell surface receptor for transforming growth factor-β and a first peptide subunit of an α-helical coiled-coil; and a second fusion protein comprised of an extracellular domain of a cell surface receptor for transforming growth factor-β and a second peptide subunit of an α-helical coiled-coil, the dimer protein having an $IC_{50}$ for inhibition of transforming growth factor-β binding and signalling activity in a nM range.

11. The coiled-coil protein of claim 10, wherein the first and second fusion proteins are comprised of the same extracellular domain of a cell surface receptor for transforming growth factor-β.

12. The coiled-coil protein of claim 10, wherein the first and second fusion proteins are comprised of different extracellular domains of a cell surface receptor for transforming growth factor-β.

13. The coiled-coil protein of claim 10, wherein said extracellular domain of a cell surface receptor is selected from the group consisting of transforming growth factor-β type II and transforming growth factor-β type III.

14. The coiled-coil protein of claim 10, wherein said first peptide subunit of the α-helical coiled-coil has a sequence identified herein as SEQ ID NO:8.

15. The coiled-coil protein of claim 10, wherein said second peptide subunit of the α-helical coiled-coil has a sequence identified herein as SEQ ID NO:5.

16. A kit comprising (i) a coiled-coil protein according to claim 10; (ii) a ligand having binding activity with the extracellular domain of the first and/or second fusion protein, said ligand being capable of detection; and (iii) instructions for use.

* * * * *

SEQUENCE LISTING

<160> NUMBER OF SEQ ID NOS: 37

<210> SEQ ID NO 1
<211> LENGTH: 224
<212> TYPE: PRT
<213> ORGANISM: Artificial
<220> FEATURE:
<223> OTHER INFORMATION: synthetic fusion protein

<400> SEQUENCE: 1

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly Glu Val Ser Ala Leu Glu Lys Glu Val Ser Ala
            180                 185                 190

Leu Glu Lys Glu Val Ser Ala Leu Glu Lys Glu Val Ser Ala Leu Glu
        195                 200                 205

Lys Glu Val Ser Ala Leu Glu Lys Gly Gly His His His His His His
    210                 215                 220

<210> SEQ ID NO 2
<211> LENGTH: 170
<212> TYPE: PRT
<213> ORGANISM: Artificial
<220> FEATURE:
<223> OTHER INFORMATION: synthetic

<400> SEQUENCE: 2

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser

```
                65                  70                  75                  80
Asn Cys Ser Ile Thr Ser Ile Cys Glu Lys Pro Gln Glu Val Cys Val
                    85                  90                  95

Ala Val Trp Arg Lys Asn Asp Glu Asn Ile Thr Leu Glu Thr Val Cys
                100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp
                165                 170

<210> SEQ ID NO 3
<211> LENGTH: 10
<212> TYPE: PRT
<213> ORGANISM: Artificial
<220> FEATURE:
<223> OTHER INFORMATION: synthetic myc tag

<400> SEQUENCE: 3

Glu Gln Lys Leu Ile Ser Glu Glu Asp Leu
1               5                   10

<210> SEQ ID NO 4
<211> LENGTH: 11
<212> TYPE: PRT
<213> ORGANISM: Artificial
<220> FEATURE:
<223> OTHER INFORMATION: synthetic linker

<400> SEQUENCE: 4

Gly Gly Arg Gly Gly Gly Ser Gly Gly Gly
1               5                   10

<210> SEQ ID NO 5
<211> LENGTH: 35
<212> TYPE: PRT
<213> ORGANISM: Artificial
<220> FEATURE:
<223> OTHER INFORMATION: E coil subunit of a coiled-coil heterodimer

<400> SEQUENCE: 5

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 6
<211> LENGTH: 8
<212> TYPE: PRT
<213> ORGANISM: Artificial
<220> FEATURE:
<223> OTHER INFORMATION: synthetic histidine tag plus two glycines

<400> SEQUENCE: 6

Gly Gly His His His His His His
1               5
```

<210> SEQ ID NO 7
<211> LENGTH: 224
<212> TYPE: PRT
<213> ORGANISM: Artificial
<220> FEATURE:
<223> OTHER INFORMATION: synthetic fusion protein

<400> SEQUENCE: 7

```
Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly
                165                 170                 175

Gly Ser Gly Gly Gly Lys Val Ser Ala Leu Lys Glu Lys Val Ser Ala
            180                 185                 190

Leu Lys Glu Lys Val Ser Ala Leu Lys Glu Lys Val Ser Ala Leu Lys
        195                 200                 205

Glu Lys Val Ser Ala Leu Lys Glu Gly Gly His His His His His
    210                 215                 220
```

<210> SEQ ID NO 8
<211> LENGTH: 35
<212> TYPE: PRT
<213> ORGANISM: Artificial
<220> FEATURE:
<223> OTHER INFORMATION: K coil subunit of the coiled-coil heterodimer

<400> SEQUENCE: 8

```
Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35
```

<210> SEQ ID NO 9
<211> LENGTH: 296
<212> TYPE: PRT
<213> ORGANISM: Artificial
<220> FEATURE:
<223> OTHER INFORMATION: synthetic fusion protein

<400> SEQUENCE: 9

```
Met Ala Val Thr Ser His His Met Ile Pro Val Met Val Leu Met
1               5                   10                  15

Ser Ala Cys Leu Ala Thr Ala Gly Pro Glu Gln Lys Leu Ile Ser Glu
                20                  25                  30

Glu Asp Leu Arg Gln Leu Arg Asn Pro Ser Gly Phe Gln Gly Gln Leu
                35                  40                  45

Asp Gly Asn Ala Thr Phe Asn Met Glu Leu Tyr Asn Thr Asp Leu Phe
50                  55                  60

Leu Val Pro Ser Pro Gly Val Phe Ser Val Ala Glu Asn Glu His Val
65                  70                  75                  80

Tyr Val Glu Val Ser Val Thr Lys Ala Asp Gln Asp Leu Gly Phe Ala
                85                  90                  95

Ile Gln Thr Cys Phe Leu Ser Pro Tyr Ser Asn Pro Asp Arg Met Ser
                100                 105                 110

Asp Tyr Thr Ile Ile Glu Asn Ile Cys Pro Lys Asp Asp Ser Val Lys
                115                 120                 125

Phe Tyr Ser Ser Lys Arg Val His Phe Pro Ile Pro His Ala Glu Val
130                 135                 140

Asp Lys Lys Arg Phe Ser Phe Leu Phe Lys Ser Val Phe Asn Thr Ser
145                 150                 155                 160

Leu Leu Phe Leu His Cys Glu Leu Thr Leu Cys Ser Arg Lys Lys Gly
                165                 170                 175

Ser Leu Lys Leu Pro Arg Cys Val Thr Pro Asp Asp Ala Cys Thr Ser
                180                 185                 190

Leu Asp Ala Thr Met Ile Trp Thr Met Met Gln Asn Lys Lys Thr Phe
                195                 200                 205

Thr Lys Pro Leu Ala Val Val Leu Gln Val Asp Tyr Lys Glu Asn Val
                210                 215                 220

Pro Ser Thr Lys Asp Ser Ser Pro Ile Pro Pro Pro Pro Gln Ile
225                 230                 235                 240

Phe His Gly Gly Arg Gly Gly Gly Ser Gly Gly Gly Lys Val Ser
                245                 250                 255

Ala Leu Lys Glu Lys Val Ser Ala Leu Lys Glu Lys Val Ser Ala Leu
                260                 265                 270

Lys Glu Lys Val Ser Ala Leu Lys Glu Lys Val Ser Ala Leu Lys Glu
                275                 280                 285

Gly Gly His His His His His His
        290                 295

<210> SEQ ID NO 10
<211> LENGTH: 242
<212> TYPE: PRT
<213> ORGANISM: Artificial
<220> FEATURE:
<223> OTHER INFORMATION: synthetic peptide

<400> SEQUENCE: 10

Met Ala Val Thr Ser His His Met Ile Pro Val Met Val Leu Met
1               5                   10                  15

Ser Ala Cys Leu Ala Thr Ala Gly Pro Glu Gln Lys Leu Ile Ser Glu
                20                  25                  30

Glu Asp Leu Arg Gln Leu Arg Asn Pro Ser Gly Phe Gln Gly Gln Leu
                35                  40                  45

Asp Gly Asn Ala Thr Phe Asn Met Glu Leu Tyr Asn Thr Asp Leu Phe
50                  55                  60
```

```
Leu Val Pro Ser Pro Gly Val Phe Ser Val Ala Glu Asn Glu His Val
 65                  70                  75                  80

Tyr Val Glu Val Ser Val Thr Lys Ala Asp Gln Asp Leu Gly Phe Ala
                 85                  90                  95

Ile Gln Thr Cys Phe Leu Ser Pro Tyr Ser Asn Pro Asp Arg Met Ser
            100                 105                 110

Asp Tyr Thr Ile Ile Glu Asn Ile Cys Pro Lys Asp Asp Ser Val Lys
        115                 120                 125

Phe Tyr Ser Ser Lys Arg Val His Phe Pro Ile Pro His Ala Glu Val
    130                 135                 140

Asp Lys Lys Arg Phe Ser Phe Leu Phe Lys Ser Val Phe Asn Thr Ser
145                 150                 155                 160

Leu Leu Phe Leu His Cys Glu Leu Thr Leu Cys Ser Arg Lys Lys Gly
                165                 170                 175

Ser Leu Lys Leu Pro Arg Cys Val Thr Pro Asp Asp Ala Cys Thr Ser
            180                 185                 190

Leu Asp Ala Thr Met Ile Trp Thr Met Met Gln Asn Lys Lys Thr Phe
        195                 200                 205

Thr Lys Pro Leu Ala Val Val Leu Gln Val Asp Tyr Lys Glu Asn Val
210                 215                 220

Pro Ser Thr Lys Asp Ser Ser Pro Ile Pro Pro Pro Pro Gln Ile
225                 230                 235                 240

Phe His

<210> SEQ ID NO 11
<211> LENGTH: 7
<212> TYPE: PRT
<213> ORGANISM: Artificial
<220> FEATURE:
<223> OTHER INFORMATION: heptad repeat used in the E coil subunit of
      SEQ ID NO:5

<400> SEQUENCE: 11

Glu Val Ser Ala Leu Glu Lys
1               5

<210> SEQ ID NO 12
<211> LENGTH: 7
<212> TYPE: PRT
<213> ORGANISM: Artificial
<220> FEATURE:
<223> OTHER INFORMATION: heptad repeat for an E coil subunit of a
      coiled-coil dimer

<400> SEQUENCE: 12

Glu Val Ser Ala Leu Glu Cys
1               5

<210> SEQ ID NO 13
<211> LENGTH: 7
<212> TYPE: PRT
<213> ORGANISM: Artificial
<220> FEATURE:
<223> OTHER INFORMATION: heptad repeat for an E coil subunit of a
      coiled-coil dimer

<400> SEQUENCE: 13

Glu Val Glu Ala Leu Glu Lys
1               5
```

```
<210> SEQ ID NO 14
<211> LENGTH: 7
<212> TYPE: PRT
<213> ORGANISM: Artificial
<220> FEATURE:
<223> OTHER INFORMATION: heptad repeat for an E coil subunit of a
      coiled-coil dimer

<400> SEQUENCE: 14

Glu Val Glu Ala Leu Gln Lys
1               5

<210> SEQ ID NO 15
<211> LENGTH: 7
<212> TYPE: PRT
<213> ORGANISM: Artificial
<220> FEATURE:
<223> OTHER INFORMATION: heptad repeat used in the K coil subunit of
      SEQ ID NO:8

<400> SEQUENCE: 15

Lys Val Ser Ala Leu Lys Glu
1               5

<210> SEQ ID NO 16
<211> LENGTH: 7
<212> TYPE: PRT
<213> ORGANISM: Artificial
<220> FEATURE:
<223> OTHER INFORMATION: heptad repeat for a K coil subunit of a
      coiled-coil dimer

<400> SEQUENCE: 16

Lys Val Ser Ala Leu Lys Cys
1               5

<210> SEQ ID NO 17
<211> LENGTH: 7
<212> TYPE: PRT
<213> ORGANISM: Artificial
<220> FEATURE:
<223> OTHER INFORMATION: heptad repeat for an E coil subunit of a
      coiled-coil dimer

<400> SEQUENCE: 17

Lys Val Glu Ala Leu Lys Lys
1               5

<210> SEQ ID NO 18
<211> LENGTH: 35
<212> TYPE: PRT
<213> ORGANISM: Artificial
<220> FEATURE:
<223> OTHER INFORMATION: E coil subunit peptide

<400> SEQUENCE: 18

Glu Val Glu Ala Leu Gln Lys Glu Val Ser Ala Leu Glu Lys Glu Val
1               5                   10                  15
Ser Ala Leu Glu Cys Glu Val Ser Ala Leu Glu Lys Glu Val Ser Ala
            20                  25                  30
Leu Gln Lys
        35

<210> SEQ ID NO 19
<211> LENGTH: 35
<212> TYPE: PRT
<213> ORGANISM: Artificial
```

```
<220> FEATURE:
<223> OTHER INFORMATION: K coil subunit peptide having 5 heptad units

<400> SEQUENCE: 19

Lys Val Glu Ala Leu Lys Lys Val Ser Ala Leu Lys Glu Lys Val
1               5                   10                  15

Ser Ala Leu Lys Cys Lys Val Ser Ala Leu Lys Glu Lys Val Glu Ala
                20                  25                  30

Leu Lys Lys
        35

<210> SEQ ID NO 20
<211> LENGTH: 38
<212> TYPE: PRT
<213> ORGANISM: Artificial
<220> FEATURE:
<223> OTHER INFORMATION: K coil subunit of the coiled-coil heterodimer
      with additional Cys and Gly residues at the N-terminus

<400> SEQUENCE: 20

Cys Gly Gly Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
                20                  25                  30

Val Ser Ala Leu Lys Glu
        35

<210> SEQ ID NO 21
<211> LENGTH: 430
<212> TYPE: PRT
<213> ORGANISM: Artificial
<220> FEATURE:
<223> OTHER INFORMATION: fusion protein comprised of the cytoplasmic
      domain of the TGF-beta receptor II joined by glycine linkers to
      an E coil subunit (SEQ ID NO:5)

<400> SEQUENCE: 21

Met His Leu Ala Ser Gly Gly Gly Gly Glu Val Ser Ala Leu Glu
1               5                   10                  15

Lys Glu Val Ser Ala Leu Glu Lys Glu Val Ser Ala Leu Glu Lys Glu
                20                  25                  30

Val Ser Ala Leu Glu Lys Glu Val Ser Ala Leu Glu Lys Gly Gly Gly
        35                  40                  45

Gly Ser Leu Glu Arg Val Asn Arg Gln Gln Lys Leu Ser Ser Thr Trp
50                  55                  60

Glu Thr Gly Lys Thr Arg Lys Leu Met Glu Phe Ser Glu His Cys Ala
65                  70                  75                  80

Ile Ile Leu Glu Asp Asp Arg Ser Asp Ile Ser Ser Thr Cys Ala Asn
                85                  90                  95

Asn Ile Asn His Asn Thr Glu Leu Leu Pro Ile Glu Leu Asp Thr Leu
                100                 105                 110

Val Gly Lys Gly Arg Phe Ala Glu Val Tyr Lys Ala Lys Leu Lys Gln
        115                 120                 125

Asn Thr Ser Glu Gln Phe Glu Thr Val Ala Val Lys Ile Phe Pro Tyr
        130                 135                 140

Glu Glu Tyr Ala Ser Trp Lys Thr Glu Lys Asp Ile Phe Ser Asp Ile
145                 150                 155                 160

Asn Leu Lys His Glu Asn Ile Leu Gln Phe Leu Thr Ala Glu Glu Arg
                165                 170                 175
```

```
Lys Thr Glu Leu Gly Lys Gln Tyr Trp Leu Ile Thr Ala Phe His Ala
            180                 185                 190

Lys Gly Asn Leu Gln Glu Tyr Leu Thr Arg His Val Ile Ser Trp Glu
        195                 200                 205

Asp Leu Arg Lys Leu Gly Ser Ser Leu Ala Arg Gly Ile Ala His Leu
    210                 215                 220

His Ser Asp His Thr Pro Cys Gly Arg Pro Lys Met Pro Ile Val His
225                 230                 235                 240

Arg Asp Leu Lys Ser Ser Asn Ile Leu Val Lys Asn Asp Leu Thr Cys
                245                 250                 255

Cys Leu Cys Asp Phe Gly Leu Ser Leu Arg Leu Asp Pro Thr Leu Ser
            260                 265                 270

Val Asp Asp Leu Ala Asn Ser Gly Gln Val Gly Thr Ala Arg Tyr Met
        275                 280                 285

Ala Pro Glu Val Leu Glu Ser Arg Met Asn Leu Glu Asn Ala Glu Ser
    290                 295                 300

Phe Lys Gln Thr Asp Val Tyr Ser Met Ala Leu Val Leu Trp Glu Met
305                 310                 315                 320

Thr Ser Arg Cys Asn Ala Val Gly Glu Val Lys Asp Tyr Glu Pro Pro
                325                 330                 335

Phe Gly Ser Lys Val Arg Glu His Pro Cys Val Glu Ser Met Lys Asp
            340                 345                 350

Asn Val Leu Arg Asp Arg Gly Arg Pro Glu Ile Pro Ser Phe Trp Leu
        355                 360                 365

Asn His Gln Gly Ile Gln Met Val Cys Glu Thr Leu Thr Glu Cys Trp
    370                 375                 380

Asp His Asp Pro Glu Ala Arg Leu Thr Ala Gln Cys Val Ala Glu Arg
385                 390                 395                 400

Phe Ser Glu Leu Glu His Leu Asp Arg Leu Ser Gly Arg Ser Cys Ser
                405                 410                 415

Glu Glu Lys Ile Pro Glu Asp Gly Ser Leu Asn Thr Thr Lys
            420                 425                 430

<210> SEQ ID NO 22
<211> LENGTH: 407
<212> TYPE: PRT
<213> ORGANISM: Artificial
<220> FEATURE:
<223> OTHER INFORMATION: synthetic fusion protein

<400> SEQUENCE: 22

Met His Leu Ala Ser Gly Gly Gly Gly Lys Val Ser Ala Leu Lys
1               5                   10                  15

Glu Lys Val Ser Ala Leu Lys Glu Lys Val Ser Ala Leu Lys Glu Lys
                20                  25                  30

Val Ser Ala Leu Lys Glu Lys Val Ser Ala Leu Lys Glu Gly Gly Gly
            35                  40                  45

Gly Ser Leu Glu His Asn Arg Thr Val Ile His His Arg Val Pro Asn
        50                  55                  60

Glu Glu Asp Pro Ser Leu Asp Arg Pro Phe Ile Ser Glu Gly Thr Thr
65                  70                  75                  80

Leu Lys Asp Leu Ile Tyr Asp Met Thr Thr Ser Gly Ser Gly Ser Gly
                85                  90                  95

Leu Pro Leu Leu Val Gln Arg Thr Ile Ala Arg Thr Ile Val Leu Gln
            100                 105                 110
```

-continued

```
Glu Ser Ile Gly Lys Gly Arg Phe Gly Glu Val Trp Arg Gly Lys Trp
        115                 120                 125

Arg Gly Glu Glu Val Ala Val Lys Ile Phe Ser Ser Arg Glu Glu Arg
    130                 135                 140

Ser Trp Phe Arg Glu Ala Glu Ile Tyr Gln Thr Val Met Leu Arg His
145                 150                 155                 160

Glu Asn Ile Leu Gly Phe Ile Ala Ala Asp Asn Lys Asp Asn Gly Thr
                165                 170                 175

Trp Thr Gln Leu Trp Leu Val Ser Asp Tyr His Glu His Gly Ser Leu
            180                 185                 190

Phe Asp Tyr Leu Asn Arg Tyr Thr Val Thr Val Glu Gly Met Ile Lys
        195                 200                 205

Leu Ala Leu Ser Thr Ala Ser Gly Leu Ala His Leu His Met Glu Ile
    210                 215                 220

Val Gly Thr Gln Gly Lys Pro Ala Ile Ala His Arg Asp Leu Lys Ser
225                 230                 235                 240

Lys Asn Ile Leu Val Lys Lys Asn Gly Thr Cys Cys Ile Ala Asp Leu
                245                 250                 255

Gly Leu Ala Val Arg His Asp Ser Ala Thr Asp Thr Ile Asp Ile Ala
            260                 265                 270

Pro Asn His Arg Val Gly Thr Lys Arg Tyr Met Ala Pro Glu Val Leu
        275                 280                 285

Asp Asp Ser Ile Asn Met Lys His Phe Glu Ser Phe Lys Arg Ala Asp
290                 295                 300

Ile Tyr Ala Met Gly Leu Val Phe Trp Glu Ile Ala Arg Arg Cys Ser
305                 310                 315                 320

Ile Gly Gly Ile His Glu Asp Tyr Gln Leu Pro Tyr Tyr Asp Leu Val
                325                 330                 335

Pro Ser Asp Pro Ser Val Glu Glu Met Arg Lys Val Val Cys Glu Gln
            340                 345                 350

Lys Leu Arg Pro Asn Ile Pro Asn Arg Trp Gln Ser Cys Glu Ala Leu
        355                 360                 365

Arg Val Met Ala Lys Ile Met Arg Glu Cys Trp Tyr Ala Asn Gly Ala
370                 375                 380

Ala Arg Leu Thr Ala Leu Arg Ile Lys Lys Thr Leu Ser Gln Leu Ser
385                 390                 395                 400

Gln Gln Glu Gly Ile Lys Met
                405
```

<210> SEQ ID NO 23
<211> LENGTH: 28
<212> TYPE: DNA
<213> ORGANISM: Artificial
<220> FEATURE:
<223> OTHER INFORMATION: primer

<400> SEQUENCE: 23
tagagcggcc gcggtggcaa ggtatccg       28

<210> SEQ ID NO 24
<211> LENGTH: 46
<212> TYPE: DNA
<213> ORGANISM: Artificial
<220> FEATURE:
<223> OTHER INFORMATION: primer

<400> SEQUENCE: 24

```
taggatccct aatggtgatg atggtgatga ccgccctctt taagtg                    46
```

<210> SEQ ID NO 25
<211> LENGTH: 33
<212> TYPE: DNA
<213> ORGANISM: Artificial
<220> FEATURE:
<223> OTHER INFORMATION: primer

<400> SEQUENCE: 25

```
atgctagcgt tggagagatg gcagtgacat ccc                                  33
```

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26

```
tagagcggcc gccatggaaa atctgtggag g                                    31
```

<210> SEQ ID NO 27
<211> LENGTH: 36
<212> TYPE: DNA
<213> ORGANISM: Artificial
<220> FEATURE:
<223> OTHER INFORMATION: primer

<400> SEQUENCE: 27

```
atgctagcca ccatgggagg tggtggtggc gaggta                               36
```

<210> SEQ ID NO 28
<211> LENGTH: 49
<212> TYPE: DNA
<213> ORGANISM: Artificial
<220> FEATURE:
<223> OTHER INFORMATION: primer

<400> SEQUENCE: 28

```
gaagctttca gtgatggtga tggtgatgtt tggtagtgtt tagggagcc                 49
```

<210> SEQ ID NO 29
<211> LENGTH: 36
<212> TYPE: DNA
<213> ORGANISM: Artificial
<220> FEATURE:
<223> OTHER INFORMATION: primer

<400> SEQUENCE: 29

```
atgctagcca ccatgggagg tggtggtggc aaggta                               36
```

<210> SEQ ID NO 30
<211> LENGTH: 47
<212> TYPE: DNA
<213> ORGANISM: Artificial
<220> FEATURE:
<223> OTHER INFORMATION: primer

<400> SEQUENCE: 30

```
cgaagctttc agtgatggtg atggtgatgc attttgatgc cttcctg                   47
```

<210> SEQ ID NO 31
<211> LENGTH: 596
<212> TYPE: PRT
<213> ORGANISM: Artificial

```
<220> FEATURE:
<223> OTHER INFORMATION: synthetic fusion protein

<400> SEQUENCE: 31

Met Gly Gly Gly Gly Lys Val Ser Ala Leu Lys Glu Lys Val Ser
1               5                   10                  15

Ala Leu Lys Glu Lys Val Ser Ala Leu Lys Glu Lys Val Ser Ala Leu
            20                  25                  30

Lys Glu Lys Val Ser Ala Leu Lys Glu Gly Gly Gly Ser Leu Glu
            35                  40                  45

Arg Arg Arg His Ile Val Arg Lys Arg Thr Leu Arg Arg Leu Leu Gln
50                      55                  60

Glu Arg Glu Leu Val Glu Pro Leu Thr Pro Ser Gly Glu Ala Pro Asn
65                  70                  75                  80

Gln Ala Leu Leu Arg Ile Leu Lys Glu Thr Glu Phe Lys Lys Ile Lys
                85                  90                  95

Val Leu Gly Ser Gly Ala Phe Gly Thr Val Tyr Lys Gly Leu Trp Ile
            100                 105                 110

Pro Glu Gly Glu Lys Val Lys Ile Pro Val Ala Ile Lys Glu Leu Arg
        115                 120                 125

Glu Ala Thr Ser Pro Lys Ala Asn Lys Glu Ile Leu Asp Glu Ala Tyr
    130                 135                 140

Val Met Ala Ser Val Asp Asn Pro His Val Cys Arg Leu Leu Gly Ile
145                 150                 155                 160

Cys Leu Thr Ser Thr Val Gln Leu Ile Thr Gln Leu Met Pro Phe Gly
                165                 170                 175

Cys Leu Leu Asp Tyr Val Arg Glu His Lys Asp Asn Ile Gly Ser Gln
            180                 185                 190

Tyr Leu Leu Asn Trp Cys Val Gln Ile Ala Lys Gly Met Asn Tyr Leu
        195                 200                 205

Glu Asp Arg Arg Leu Val His Arg Asp Leu Ala Ala Arg Asn Val Leu
    210                 215                 220

Val Lys Thr Pro Gln His Val Lys Ile Thr Asp Phe Gly Leu Ala Lys
225                 230                 235                 240

Leu Leu Gly Ala Glu Glu Lys Glu Tyr His Ala Glu Gly Gly Lys Val
                245                 250                 255

Pro Ile Lys Trp Met Ala Leu Glu Ser Ile Leu His Arg Ile Tyr Thr
            260                 265                 270

His Gln Ser Asp Val Trp Ser Tyr Gly Val Thr Val Trp Glu Leu Met
        275                 280                 285

Thr Phe Gly Ser Lys Pro Tyr Asp Gly Ile Pro Ala Ser Glu Ile Ser
    290                 295                 300

Ser Ile Leu Glu Lys Gly Glu Arg Leu Pro Gln Pro Ile Cys Thr
305                 310                 315                 320

Ile Asp Val Tyr Met Ile Met Val Lys Cys Trp Met Ile Asp Ala Asp
                325                 330                 335

Ser Arg Pro Lys Phe Arg Glu Leu Ile Ile Glu Phe Ser Lys Met Ala
            340                 345                 350

Arg Asp Pro Gln Arg Tyr Leu Val Ile Gln Gly Asp Glu Arg Met His
        355                 360                 365

Leu Pro Ser Pro Thr Asp Ser Asn Phe Tyr Arg Ala Leu Met Asp Glu
    370                 375                 380

Glu Asp Met Asp Asp Val Val Asp Ala Asp Glu Tyr Leu Ile Pro Gln
385                 390                 395                 400
```

```
Gln Gly Phe Phe Ser Ser Pro Ser Thr Ser Arg Thr Pro Leu Leu Ser
                405                 410                 415

Ser Leu Ser Ala Thr Ser Asn Asn Ser Thr Val Ala Cys Ile Asp Arg
            420                 425                 430

Asn Gly Leu Gln Ser Cys Pro Ile Lys Glu Asp Ser Phe Leu Gln Arg
        435                 440                 445

Tyr Ser Ser Asp Pro Thr Gly Ala Leu Thr Glu Asp Ser Ile Asp Asp
    450                 455                 460

Thr Phe Leu Pro Val Pro Glu Tyr Ile Asn Gln Ser Val Pro Lys Arg
465                 470                 475                 480

Pro Ala Gly Ser Val Gln Asn Pro Val Tyr His Asn Gln Pro Leu Asn
                485                 490                 495

Pro Ala Pro Ser Arg Asp Pro His Tyr Gln Asp Pro His Ser Thr Ala
            500                 505                 510

Val Gly Asn Pro Glu Tyr Leu Asn Thr Val Gln Pro Thr Cys Val Asn
        515                 520                 525

Ser Thr Phe Asp Ser Pro Ala His Trp Ala Gln Lys Gly Ser His Gln
    530                 535                 540

Ile Ser Leu Asp Asn Pro Asp Tyr Gln Gln Asp Phe Phe Pro Lys Glu
545                 550                 555                 560

Ala Lys Pro Asn Gly Ile Phe Lys Gly Ser Thr Ala Glu Asn Ala Glu
                565                 570                 575

Tyr Leu Arg Val Ala Pro Gln Ser Ser Glu Phe Ile Gly Ala His His
            580                 585                 590

His His His His
        595

<210> SEQ ID NO 32
<211> LENGTH: 6
<212> TYPE: PRT
<213> ORGANISM: Artificial
<220> FEATURE:
<223> OTHER INFORMATION: synthetic linker

<400> SEQUENCE: 32

Met Gly Gly Gly Gly Gly
1               5

<210> SEQ ID NO 33
<211> LENGTH: 7
<212> TYPE: PRT
<213> ORGANISM: Artificial
<220> FEATURE:
<223> OTHER INFORMATION: synthetic linker

<400> SEQUENCE: 33

Gly Gly Gly Gly Ser Leu Glu
1               5

<210> SEQ ID NO 34
<211> LENGTH: 596
<212> TYPE: PRT
<213> ORGANISM: Artificial
<220> FEATURE:
<223> OTHER INFORMATION: synthetic fusion protein

<400> SEQUENCE: 34

Met Gly Gly Gly Gly Gly Glu Val Ser Ala Leu Glu Lys Glu Val Ser
1               5                   10                  15
```

```
Ala Leu Glu Lys Glu Val Ser Ala Leu Glu Lys Glu Val Ser Ala Leu
             20                  25                  30
Glu Lys Glu Val Ser Ala Leu Glu Lys Gly Gly Gly Ser Leu Glu
             35                  40                  45
Arg Arg Arg His Ile Val Arg Lys Arg Thr Leu Arg Arg Leu Leu Gln
 50                      55                  60
Glu Arg Glu Leu Val Glu Pro Leu Thr Pro Ser Gly Glu Ala Pro Asn
 65                  70                  75                   80
Gln Ala Leu Leu Arg Ile Leu Lys Glu Thr Glu Phe Lys Lys Ile Lys
                 85                  90                  95
Val Leu Gly Ser Gly Ala Phe Gly Thr Val Tyr Lys Gly Leu Trp Ile
                100                 105                 110
Pro Glu Gly Glu Lys Val Lys Ile Pro Val Ala Ile Lys Glu Leu Arg
                115                 120                 125
Glu Ala Thr Ser Pro Lys Ala Asn Lys Glu Ile Leu Asp Glu Ala Tyr
            130                 135                 140
Val Met Ala Ser Val Asp Asn Pro His Val Cys Arg Leu Leu Gly Ile
145                 150                 155                 160
Cys Leu Thr Ser Thr Val Gln Leu Ile Thr Gln Leu Met Pro Phe Gly
                165                 170                 175
Cys Leu Leu Asp Tyr Val Arg Glu His Lys Asp Asn Ile Gly Ser Gln
                180                 185                 190
Tyr Leu Leu Asn Trp Cys Val Gln Ile Ala Lys Gly Met Asn Tyr Leu
                195                 200                 205
Glu Asp Arg Arg Leu Val His Arg Asp Leu Ala Ala Arg Asn Val Leu
 210                 215                 220
Val Lys Thr Pro Gln His Val Lys Ile Thr Asp Phe Gly Leu Ala Lys
225                 230                 235                 240
Leu Leu Gly Ala Glu Glu Lys Glu Tyr His Ala Glu Gly Gly Lys Val
                245                 250                 255
Pro Ile Lys Trp Met Ala Leu Glu Ser Ile Leu His Arg Ile Tyr Thr
                260                 265                 270
His Gln Ser Asp Val Trp Ser Tyr Gly Val Thr Val Trp Glu Leu Met
            275                 280                 285
Thr Phe Gly Ser Lys Pro Tyr Asp Gly Ile Pro Ala Ser Glu Ile Ser
        290                 295                 300
Ser Ile Leu Glu Lys Gly Glu Arg Leu Pro Gln Pro Pro Ile Cys Thr
305                 310                 315                 320
Ile Asp Val Tyr Met Ile Met Val Lys Cys Trp Met Ile Asp Ala Asp
                325                 330                 335
Ser Arg Pro Lys Phe Arg Glu Leu Ile Ile Glu Phe Ser Lys Met Ala
            340                 345                 350
Arg Asp Pro Gln Arg Tyr Leu Val Ile Gln Gly Asp Glu Arg Met His
            355                 360                 365
Leu Pro Ser Pro Thr Asp Ser Asn Phe Tyr Arg Ala Leu Met Asp Glu
        370                 375                 380
Glu Asp Met Asp Asp Val Val Asp Ala Asp Glu Tyr Leu Ile Pro Gln
385                 390                 395                 400
Gln Gly Phe Phe Ser Ser Pro Ser Thr Ser Arg Thr Pro Leu Leu Ser
                405                 410                 415
Ser Leu Ser Ala Thr Ser Asn Asn Ser Thr Val Ala Cys Ile Asp Arg
            420                 425                 430
Asn Gly Leu Gln Ser Cys Pro Ile Lys Glu Asp Ser Phe Leu Gln Arg
```

```
                  435                 440                 445
        Tyr Ser Ser Asp Pro Thr Gly Ala Leu Thr Glu Asp Ser Ile Asp Asp
            450                 455                 460

Thr Phe Leu Pro Val Pro Glu Tyr Ile Asn Gln Ser Val Pro Lys Arg
        465                 470                 475                 480

Pro Ala Gly Ser Val Gln Asn Pro Val Tyr His Asn Gln Pro Leu Asn
                            485                 490                 495

Pro Ala Pro Ser Arg Asp Pro His Tyr Gln Asp Pro His Ser Thr Ala
                        500                 505                 510

Val Gly Asn Pro Glu Tyr Leu Asn Thr Val Gln Pro Thr Cys Val Asn
                    515                 520                 525

Ser Thr Phe Asp Ser Pro Ala His Trp Ala Gln Lys Gly Ser His Gln
                530                 535                 540

Ile Ser Leu Asp Asn Pro Asp Tyr Gln Gln Asp Phe Phe Pro Lys Glu
        545                 550                 555                 560

Ala Lys Pro Asn Gly Ile Phe Lys Gly Ser Thr Ala Glu Asn Ala Glu
                            565                 570                 575

Tyr Leu Arg Val Ala Pro Gln Ser Ser Glu Phe Ile Gly Ala His His
                        580                 585                 590

His His His His
                595

<210> SEQ ID NO 35
<211> LENGTH: 32
<212> TYPE: DNA
<213> ORGANISM: Artificial
<220> FEATURE:
<223> OTHER INFORMATION: primer

<400> SEQUENCE: 35
atctcgagcg aaggcgccac atcgttcgga gg                                    32

<210> SEQ ID NO 36
<211> LENGTH: 51
<212> TYPE: DNA
<213> ORGANISM: Artificial
<220> FEATURE:
<223> OTHER INFORMATION: primer

<400> SEQUENCE: 36
gctagctcag tgatggtgat ggtgatgtgc tccaataaat tcactgcttt c               51

<210> SEQ ID NO 37
<211> LENGTH: 34
<212> TYPE: DNA
<213> ORGANISM: Artificial
<220> FEATURE:
<223> OTHER INFORMATION: primer

<400> SEQUENCE: 37
attctagaca ccatgcgaag gcgccacatc gttc                                  34
```